United States Patent
Winston et al.

(10) Patent No.: US 12,390,276 B2
(45) Date of Patent: Aug. 19, 2025

(54) SPINAL IMPLANTS AND SURGICAL PROCEDURES WITH REDUCED SUBSIDENCE, AND ASSOCIATED SYSTEMS AND METHODS

(71) Applicant: Carlsmed, Inc., Carlsbad, CA (US)

(72) Inventors: Jeremy Winston, San Diego, CA (US); Alexander Roeca, San Diego, CA (US); Elliot Calderon, Carlsbad, CA (US); Sydnee Hyman, San Diego, CA (US); Niall Patrick Casey, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 485 days.

(21) Appl. No.: 17/978,673

(22) Filed: Nov. 1, 2022

(65) Prior Publication Data
US 2023/0138162 A1    May 4, 2023

Related U.S. Application Data

(60) Provisional application No. 63/274,135, filed on Nov. 1, 2021.

(51) Int. Cl.
*A61B 34/10*    (2016.01)

(52) U.S. Cl.
CPC ........ *A61B 34/10* (2016.02); *A61B 2034/104* (2016.02); *A61B 2034/105* (2016.02)

(58) Field of Classification Search
CPC .............. A61B 34/10; A61B 2034/104; A61B 2034/105
See application file for complete search history.

(56) References Cited

U.S. PATENT DOCUMENTS

| 4,704,686 | A | 11/1987 | Aldinger |
| 4,936,862 | A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Gary Collins
(74) *Attorney, Agent, or Firm* — Perkins Coie LLP

(57) ABSTRACT

Systems and methods for designing and implementing patient-specific surgical procedures and/or medical devices are disclosed. In some embodiments, a method includes receiving a patient data set of a patient. The patient data set is compared to a plurality of reference patient data sets, wherein each of the plurality of reference patient data sets is associated with a corresponding reference patient. A subset of the plurality of reference patient data sets is selected based, at least partly, on similarity to the patient data set and treatment outcome of the corresponding reference patient. Based on the selected subset, at least one surgical procedure or medical device design for treating the patient is generated. The surgical procedure or medical device design can be generated based at least partially on one or more parameters associated with a reduced risk of one or more post-operative conditions.

54 Claims, 13 Drawing Sheets

(56) References Cited

U.S. PATENT DOCUMENTS

| | | |
|---|---|---|
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| 11,112,770 B2 | 9/2021 | Roh et al. |
| D933,692 S | 10/2021 | Smith |
| 11,166,764 B2 | 11/2021 | Roh et al. |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 11,376,076 B2 | 7/2022 | Casey et al. |
| 11,432,943 B2 | 9/2022 | Casey et al. |
| 11,439,514 B2 | 9/2022 | Casey et al. |
| 11,497,559 B1 | 11/2022 | Roh et al. |
| 2004/0104512 A1 | 6/2004 | Eidenschink |
| 2005/0234555 A1 | 10/2005 | Sutton et al. |
| 2005/0273170 A1 | 12/2005 | Navarro et al. |
| 2006/0100497 A1 | 5/2006 | Sawazaki et al. |
| 2007/0272747 A1 | 11/2007 | Woods et al. |
| 2007/0276369 A1 | 11/2007 | Allard et al. |
| 2007/0276501 A1 | 11/2007 | Betz |
| 2008/0227047 A1 | 9/2008 | Lowe |
| 2009/0062739 A1 | 3/2009 | Anderson |
| 2010/0191088 A1 | 7/2010 | Anderson et al. |
| 2010/0324692 A1 | 12/2010 | Uthgenannt |
| 2011/0196451 A1 | 8/2011 | Hill |
| 2012/0150243 A9 | 6/2012 | Crawford et al. |
| 2012/0322018 A1 | 12/2012 | Lowe |

(56) References Cited

U.S. PATENT DOCUMENTS

| | | |
|---|---|---|
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0164022 A1 | 6/2014 | Reed |
| 2014/0244220 A1* | 8/2014 | McKinnon ............ A61F 2/02 703/1 |
| 2014/0263674 A1 | 9/2014 | Cerveny |
| 2014/0277487 A1 | 9/2014 | Davenport et al. |
| 2014/0350614 A1 | 11/2014 | Frey |
| 2015/0079533 A1 | 3/2015 | Lowe |
| 2015/0089590 A1 | 3/2015 | Krishnan et al. |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0081810 A1 | 3/2016 | Reiley et al. |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0354213 A1 | 12/2016 | Cowan |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |
| 2017/0112548 A1 | 4/2017 | Alamin et al. |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0196499 A1 | 7/2017 | Hunter |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0065685 A1 | 2/2019 | Pickover |
| 2019/0069956 A1 | 3/2019 | Ryan et al. |
| 2019/0099221 A1 | 4/2019 | Schmidt et al. |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0328929 A1 | 10/2019 | Kugler et al. |
| 2019/0333622 A1 | 10/2019 | Levin |
| 2019/0354693 A1 | 11/2019 | Yoon |
| 2019/0380792 A1 | 12/2019 | Poltaretskyi et al. |
| 2019/0388131 A1 | 12/2019 | Mehl et al. |
| 2020/0021570 A1 | 1/2020 | Lin |
| 2020/0078180 A1 | 3/2020 | Casey et al. |
| 2020/0085509 A1 | 3/2020 | Roh et al. |
| 2020/0170802 A1 | 6/2020 | Casey et al. |
| 2020/0258605 A1 | 8/2020 | Blechman |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0169576 A1 | 6/2021 | Ryan et al. |
| 2021/0192759 A1 | 6/2021 | Lang |
| 2021/0210189 A1 | 7/2021 | Casey et al. |
| 2021/0287770 A1 | 9/2021 | Anderson |
| 2021/0378752 A1 | 12/2021 | Paul et al. |
| 2021/0382457 A1 | 12/2021 | Roh et al. |
| 2022/0000625 A1 | 1/2022 | Cordonnier |
| 2022/0006642 A1 | 1/2022 | Maj et al. |
| 2022/0013211 A1 | 1/2022 | Steinberg et al. |
| 2022/0039965 A1 | 2/2022 | Casey et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |
| 2022/0370142 A1 | 11/2022 | Schoenfeld et al. |
| 2022/0387191 A1 | 12/2022 | Cordonnier |
| 2022/0401150 A1 | 12/2022 | Cordonnier |
| 2022/0406452 A1 | 12/2022 | Shelton |
| 2022/0409140 A1 | 12/2022 | Cordonnier |
| 2023/0000560 A1 | 1/2023 | Roh et al. |
| 2023/0014384 A1 | 1/2023 | Cordonnier |
| 2023/0023440 A1 | 1/2023 | Casey et al. |
| 2023/0034731 A1 | 2/2023 | Cordonnier |
| 2023/0052263 A1 | 2/2023 | Casey et al. |
| 2024/0065767 A1 | 2/2024 | Cordonnier |
| 2024/0225844 A1 | 7/2024 | Casey et al. |
| 2024/0307120 A1 | 9/2024 | Casey et al. |
| 2024/0428954 A1 | 12/2024 | Casey et al. |

FOREIGN PATENT DOCUMENTS

| | | |
|---|---|---|
| CN | 204468348 U | 7/2015 |
| CN | 105796214 A | 7/2016 |
| CN | 106202861 | 12/2016 |
| CN | 107220933 | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 | 11/2021 |
| EP | 3120796 A1 | 1/2017 |
| WO | 9507509 A1 | 3/1995 |
| WO | 2004110309 A2 | 12/2004 |
| WO | 2010151564 A1 | 12/2010 |
| WO | 2012154534 A1 | 11/2012 |
| WO | 2014180972 A2 | 11/2014 |
| WO | 2016172694 A1 | 10/2016 |
| WO | 2017116346 A1 | 7/2017 |
| WO | 2019112917 A1 | 6/2019 |
| WO | 2019148154 A1 | 8/2019 |
| WO | 2019165152 A1 | 8/2019 |
| WO | 2019241167 A1 | 12/2019 |
| WO | 2020033743 A1 | 2/2020 |
| WO | 2020055874 A1 | 3/2020 |
| WO | 2021141849 A1 | 7/2021 |
| WO | 2022045956 A1 | 3/2022 |
| WO | 2022192222 A1 | 9/2022 |
| WO | 2023034405 A1 | 3/2023 |

OTHER PUBLICATIONS

Eshkalak, S.K. et al., "The role of three-dimensional printing in healthcare and medicine." Materials and Design 194, Jul. 10, 20202, 15 pages.

(56) References Cited

OTHER PUBLICATIONS

Extended European Search Report for European Application No. 18885367.5, mailed Aug. 16, 2021, 8 pages.
Extended European Search Report for European Application No. 19859930.0, mailed Jun. 22, 2022, 7 pages.
Extended European Search Report for European Application No. 19890663.8, mailed Jul. 29, 2022, 8 pages.
Harrysson, O. et al., "Custom-designed orthopedic implants evaluated using finite element analysis of patient-specific computed tomography data: femoral-component case study." BMC Musculoskeletal Disorders. Dec. 2007, 8:91, 10 pages.
International Search Report and Written Opinion for International Application No. PCT/US19/50885, mailed Jan. 28, 2020, 21 pages.
International Search Report and Written Opinion for International Application No. PCT/US19/63855, mailed Feb. 14, 2020, 15 pages.
International Search Report and Written Opinion for International Application No. PCT/US21/44878, mailed Nov. 16, 2021, 18 pages.
International Search Report and Written Opinion for International Application No. PCT/US21/45503, mailed Jan. 11, 2022, 19 pages.
International Search Report and Written Opinion for International Application No. PCT/US22/32624, mailed Oct. 28, 2022, 16 pages.
International Search Report and Written Opinion for International Application No. PCT/US22/35232, mailed Nov. 16, 2022, 24 pages.
International Search Report and Written Opinion for International Application No. PCT/US22/36007, mailed Oct. 11, 2022, 14 pages.
International Search Report and Written Opinion for International Application No. PCT/US22/37500, mailed Dec. 28, 2022, 19 pages.
International Search Report and Written Opinion for International Application No. PCT/US22/37640, mailed Nov. 15, 2022, 13 pages.
International Search Report and Written Opinion for International Application No. PCT/US22/42188, mailed Dec. 29, 2022, 19 pages.
International Search Report and Written Opinion for International Patent Application No. PCT/US2018/063530, mailed Feb. 12, 2019, 16 pages.
International Search Report and Written Opinion for International Patent Application No. PCT/US21/12065, mailed Apr. 29, 2021, 19 pages.
International Search Report and Written Opinion for International Patent Application No. PCT/US21/59837, mailed Feb. 7, 2022, 19 pages.
International Search Report and Written Opinion for International Patent Application No. PCT/US21/60074, mailed Mar. 17, 2022, 21 pages.
International Search Report and Written Opinion for International Patent Application No. PCT/US22/48536, mailed Apr. 13, 2023, 12 pages.
Majdouline et al., "Preoperative assessment and evaluation of instrumentation strategies for the treatment of adolescent idiopathic scoliosis: computer simulation and optimization." Scoliosis 7, 21 (2012), pp. 1-8.
Materialise Mimics, "Efficiently turn scans into accurate virtual 3D models," Retrieved on Nov. 1, 2019 at www.materialize.com/en/medical/software/mimics, 1 page.
Office Action for Japanese Application No. 2020-550591, mailed Dec. 26, 2022, 4 pages, English Translation.
Pimenta, Dr. Luiz, "Current Surgical Strategies to Restore Proper Sagittal Alignment," Journal of Spine 2015, vol. 4, Issue 4, 2 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 15/958,409 for Ryan, filed Apr. 21, 2017.
International Search Report and Written Opinion for International Patent Application No. PCT/US24/10934, mailed May 17, 2024, 28 pages.
International Search Report and Written Opinion for International Patent Application No. PCT/US24/109760, mailed Jul. 26, 2024, 18 pages.
Mandel et al., "Image-Guided Tethering Spine Surgery With Outcome Prediction Using Spatio-Temporal Dynamic Networks." IEEE Transactions on Medical Imaging, vol. 40, Issue 2, Feb. 2021, 12 pages.
International Search Report and Written Opinion for International Patent Application No. PCT/US24/35310, mailed Nov. 14, 2024, 16 pages.

* cited by examiner

Study Group X (410a, 412)

| PT. ID | X123 | PT. ID | Y456 | PT. ID | Z789 | PT. ID | A246 |
|---|---|---|---|---|---|---|---|
| Metric | Value | Metric | Value | Metric | Value | Metric | Value |
| Age | 56 | Age | 66 | Age | 63 | Age | 73 |
| Gender | F | Gender | F | Gender | M | Gender | M |
| BMI | 38 | BMI | 38 | BMI | 30 | BMI | 30 |
| LL | 36 | LL | 41 | LL | 39 | LL | 40 |
| PI | 51 | PI | 52 | PI | 50 | PI | 48 |
| Levels | 3 | Levels | 4 | Levels | 4 | Levels | 5 |
| Outcome | | Outcome | | Outcome | | Outcome | |
| Fused | Y | Fused | Y | Fused | Y | Fused | N |
| HRQL | A | HRQL | B | HRQL | A | HRQL | D |
| Complications | 0 | Complications | 0 | Complications | 1 | Complications | 0 |
| Surg. Intervention | | Surg. Intervention | | Surg. Intervention | | Surg. Intervention | |
| Imp. design | Stock | Imp. design | Stock | Imp. design | Stock | Imp. design | Stock |
| Imp placemt | A | Imp placemt | A | Imp placemt | B | Imp placemt | B |
| Surg. Appr. | Lat | Surg. Appr. | Ant | Surg. Appr. | Lat | Surg. Appr. | Post |

Practice Y (410b, 414)

| PT. ID | B135 | PT. ID | C468 | PT. ID | D357 | PT. ID | E468 |
|---|---|---|---|---|---|---|---|
| Metric | Value | Metric | Value | Metric | Value | Metric | Value |
| Age | 73 | Age | 60 | Age | 58 | Age | 78 |
| Gender | F | Gender | M | Gender | M | Gender | M |
| BMI | 37 | BMI | 32 | BMI | 29 | BMI | 30 |
| LL | 40 | LL | 40 | LL | 39 | LL | 40 |
| PI | 55 | PI | 55 | PI | 52 | PI | 48 |
| Levels | 4 | Levels | 4 | Levels | 4 | Levels | 3 |
| Outcome | | Outcome | | Outcome | | Outcome | |
| Fused | Y | Fused | Y | Fused | N | Fused | N |
| HRQL | A | HRQL | A | HRQL | C | HRQL | F |
| Complications | 0 | Complications | 0 | Complications | 1 | Complications | 0 |
| Surg. Intervention | | Surg. Intervention | | Surg. Intervention | | Surg. Intervention | |
| Imp. design | PS | Imp. design | PS | Imp. design | Stock | Imp. design | Stock |
| Imp placemt | A | Imp placemt | A | Imp placemt | B | Imp placemt | B |
| Surg. Appr. | Ant | Surg. Appr. | Ant,Lat | Surg. Appr. | Post | Surg. Appr. | Lat |

University Z (410d, 416)

| PT. ID | F135 | PT. ID | G468 | PT. ID | H357 | PT. ID | J468 |
|---|---|---|---|---|---|---|---|
| Metric | Value | Metric | Value | Metric | Value | Metric | Value |
| Age | 73 | Age | 60 | Age | 63 | Age | 71 |
| Gender | F | Gender | M | Gender | M | Gender | M |
| BMI | 33 | BMI | 42 | BMI | 31 | BMI | 30 |
| LL | 40 | LL | 40 | LL | 39 | LL | 40 |
| PI | 55 | PI | 55 | PI | 52 | PI | 50 |
| Levels | 4 | Levels | 4 | Levels | 4 | Levels | 3 |
| Outcome | | Outcome | | Outcome | | Outcome | |
| Fused | Y | Fused | Y | Fused | Y | Fused | N |
| HRQL | A | HRQL | A | HRQL | A | HRQL | F |
| Complications | 0 | Complications | 0 | Complications | 1 | Complications | 2 |
| Surg. Intervention | | Surg. Intervention | | Surg. Intervention | | Surg. Intervention | |
| Imp. design | PS | Imp. design | PS | Imp. design | PS | Imp. design | Stock |
| Imp placemt | A | Imp placemt | A | Imp placemt | B | Imp placemt | B |
| Surg. Appr. | Post | Surg. Appr. | Ant,Lat | Surg. Appr. | Ant,Lat | Surg. Appr. | Lat |

*FIG. 4B*

|   | Pre-op Similarity | | Outcome quotient |
|---|---|---|---|
|   | Pt. ID | Value | |
| 410a → | X123 | 9 | 1 |
|   | Y456 | 18 | 2 |
|   | Z789 | 11 | 2 |
|   | A246 | 25 | 9 |
|   | B135 | 20 | 1 |
| 410b → | C468 | 2 | 1 |
| 410c → | D357 | 5 | 9 |
|   | E468 | 30 | 10 |
|   | F135 | 16 | 1 |
|   | G468 | 12 | 1 |
| 410d → | H357 | 8 | 2 |
|   | J468 | 21 | 12 |

*FIG. 4C*

SPINAL IMPLANTS AND SURGICAL PROCEDURES WITH REDUCED SUBSIDENCE, AND ASSOCIATED SYSTEMS AND METHODS

CROSS-REFERENCE TO RELATED APPLICATION(S)

The present application claims priority to U.S. Provisional Patent Application No. 63/274,135, filed Nov. 1, 2021, the disclosure of which is incorporated by reference herein in its entirety.

TECHNICAL FIELD

The present disclosure is generally related to designing and implementing medical care, and more particularly to systems and methods for designing and implementing surgical procedures and/or medical devices with a reduced probability of subsidence.

BACKGROUND

Intervertebral interbody implants are used for a wide variety of spinal surgeries, including spinal fusion surgeries such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF), and non-fusion surgeries, such as spinal arthroplasty. A known complication of interbody implants is the subsidence of disc height during the post-operative period. This can be caused, for example, by the implant subsiding into the superior or inferior vertebral endplate, causing a reduction in disc height and space. In some embodiments, this post-operative subsidence can adversely affect the long-term clinical outcome of the surgery, the mechanical stability of the spine, or the like. Accordingly, a need exists for designing implants and treatment protocols that reduce the likelihood and/or magnitude of implant subsidence following implantation of an interbody implant.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIGS. 4A-4C illustrate exemplary data sets that may be used and/or generated in connection with the methods described herein, according to an embodiment. FIG. 4A illustrates a patient data set. FIG. 4B illustrates a plurality of reference patient data sets.

FIG. 4C illustrates similarity scores and outcome scores for the reference patient data sets of FIG. 4B.

DETAILED DESCRIPTION

A. Overview of Present Technology

Figure 1:
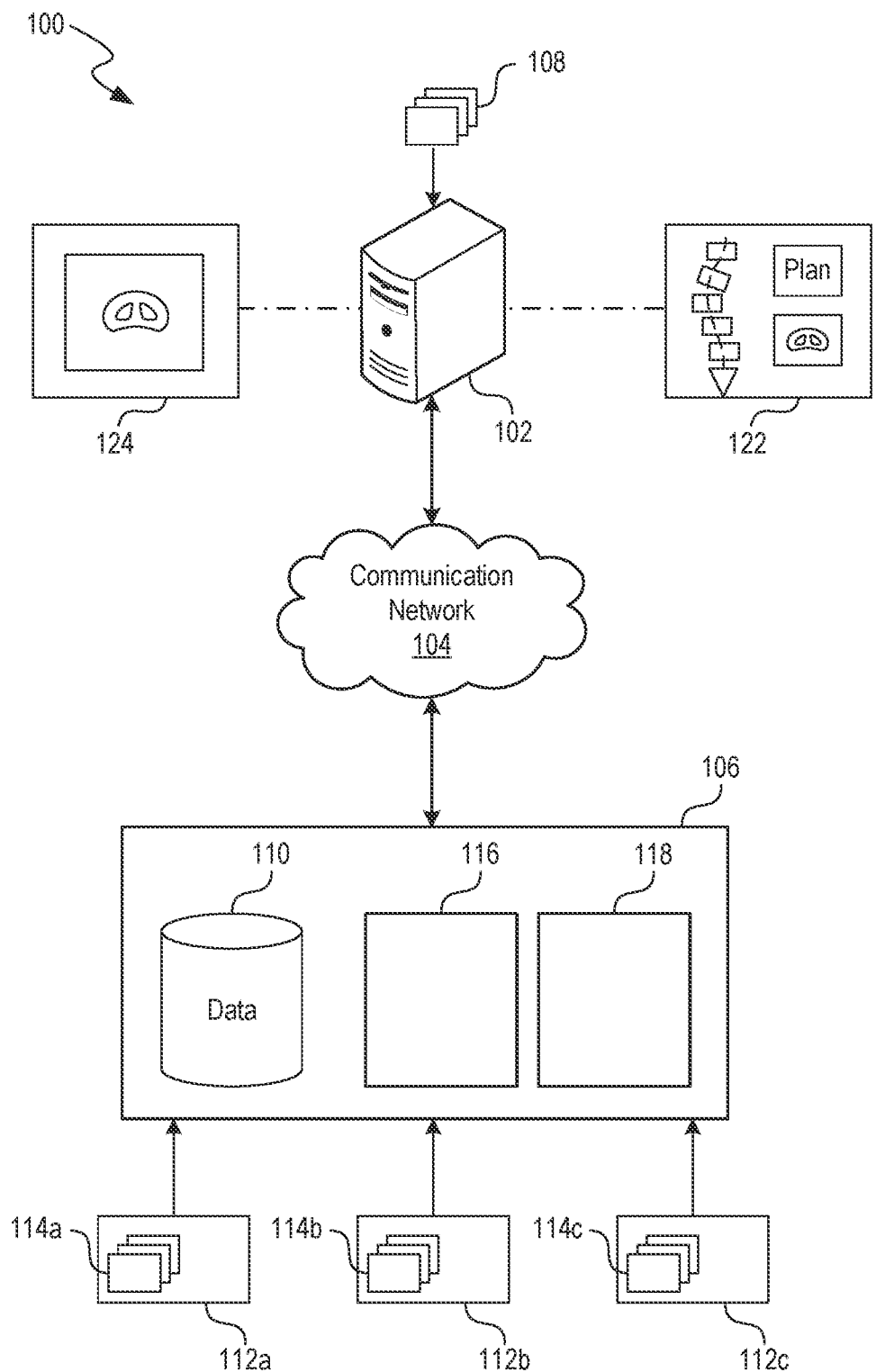
FIG. 1 is a network connection diagram illustrating a system for providing patient-specific medical care, according to an embodiment.

The present technology is directed to systems and methods for planning and implementing medical procedures and/or devices. In some embodiments, the medical devices can include orthopedic and/or intervertebral implants, and the medical procedures can include procedures for implanting the intervertebral implants in a target portion or region of a patient's spine. The medical devices and/or procedures can be at least partially designed by a computer system. The computer system can design the medical devices and/or procedures based at least partially on one or more data sets (e.g., patient data sets, reference patient data sets, etc.) and/or one or more parameters associated with a target post-operative outcome. As a specific example, the computer system can design one or more patient-specific intervertebral implants and/or one or more medical procedures for inserting each of the patient-specific implant(s) in a respective target region of a patient's spine. As described in detail below, the patient-specific intervertebral implant(s) can be specifically designed to reduce the probability and/or magnitude of implant and/or disc-height subsidence following implantation of the implants. Accordingly, the present technology is expected to improve patient treatment outcomes by reducing the likelihood and/or magnitude of disc-height collapse following implantation of an intervertebral interbody device.

In many of the embodiments disclosed herein, a method of providing medical care includes comparing a patient data set of a patient to be treated with a plurality of reference patient data sets (e.g., data from previously-treated patients).

The method can include selecting a subset of the reference patient data sets, e.g., based on similarity of the reference patient data set to the patient data set and/or whether the reference patient had a favorable treatment outcome, such as improved pain scores, no subsidence, etc. The selected subset can be used to generate a surgical procedure and/or medical device design that is likely to produce a favorable treatment outcome (e.g., improved pain scores, no subsidence, etc.) for the particular patient. In some embodiments, the selected subset is analyzed to identify correlations between patient pathology, surgical procedures, device designs, and/or treatment outcomes, and these correlations are used to determine a personalized treatment protocol with a higher likelihood of success.

In the context of orthopedic surgery, systems with improved computing capabilities (e.g., predictive analytics, machine learning, neural networks, artificial intelligence (AI)) can use large data sets to define improved or optimal surgical interventions and/or implant designs for a specific patient. The patient's entire data can be characterized and compared to aggregated data from groups of prior patients (e.g., parameters, metrics, pathologies, treatments, outcomes). In some embodiments, the systems described herein use this aggregated data to formulate potential treatment solutions (e.g., surgical plans and/or implant designs for spine and orthopedic procedures) and analyze the associated likelihood of success. These systems can further compare potential treatment solutions to determine an optimal patient-specific solution that is expected to maximize the likelihood for a successful outcome, including reducing the likelihood of implant subsidence and/or disc-height subsidence following implantation of an implant.

For example, if a patient presents with a spinal deformity pathology that can be described with data including lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters, an algorithm using these data points as inputs can be used to describe an optimal surgical plan and/or implant design to correct the subject pathology and improve the patient's outcome. Additionally, the algorithm can determine the optimal surgical plan and/or implant design so as to at least partially reduce or minimize the occurrence of one or more post-operative events or conditions. For example, the algorithm can design the implant and/or implant procedure to at least partially reduce or minimize the probability of implant subsidence. Similarly, the algorithm can design the implant and/or implant procedure to at least partially reduce or minimize the magnitude of any implant subsidence. The algorithm can design the implant, and/or can revise the design of the implant, based at least partially on one or more predictive models and/or simulations (e.g., mechanical simulations, bone growth simulations, subsidence predictions based on implant design, subsidence predictions based on vertebral properties, etc.). In some embodiments, the algorithm can design and/or revise the design of the implant based at least partially on one or more subsidence-reducing parameters (e.g., a length, a width, a contact surface area, a surface topography, a load-bearing surface position, and/or a target position of the implant, etc.). Additionally, or alternatively, the algorithm can adjust the surgical plan based at least partially on the predictive model(s) and/or simulation(s). As additional data inputs are used to describe the pathology (e.g., disc height, segment flexibility, bone quality, bone strength, bone stiffness, bone hardness, bone elastic modulus, bone growth, rotational displacement), the algorithm can use these additional inputs to further define and/or revise an optimal surgical plan and/or implant design for that particular patient and their pathology.

In some embodiments, the present technology can automatically or at least semi-automatically determine a corrected anatomical configuration for a subject patient suffering from one or more deformities. For example, the computing systems described herein can apply mathematical rules for select parameters (e.g., lumbar lordosis, Cobb angles, etc.) and/or identify similar patients by analyzing reference patient data sets, and, based on the rules and/or comparison to other patients, can provide a recommended anatomical configuration that represents the optimal outcome if the subject patient were to undergo surgery. In some embodiments, the computing systems described herein can apply threshold design criteria and/or threshold probabilities such that the determined corrected anatomical configuration at least partially reduces or minimizes the occurrence (e.g., a probability or likelihood) of one or more post-operative conditions (e.g., implant subsidence). In some embodiments, the systems and methods described herein generate a virtual model of the corrected/recommended anatomical configuration (e.g., for surgeon review).

In some embodiments, the present technology can also automatically or at least semi-automatically generate a surgical plan for achieving a previously-identified corrected anatomical configuration for a subject patient. For example, based off the virtual model of the corrected anatomical configuration, the systems and methods herein can determine a type of surgery (e.g., spinal fusion surgery, non-fusion surgery, etc.), a surgical approach (e.g., anterior, lateral, posterior, etc.), and/or spinal parameters for the corrected anatomical configuration (e.g., lumbar lordosis, Cobb angles, sagittal vertical axis, coronal displacement, etc.). The surgical plan can be transmitted to a surgeon for review and approval. In some embodiments, the present technology can also design one or more patient-specific implants for achieving the corrected anatomical configuration via the surgical plan. In some embodiments, the surgical plan and/or patient-specific implant(s) can be designed so as to at least partially reduce or minimize the occurrence and/or magnitude of one or more post-operative conditions (e.g., implant subsidence).

In some embodiments, the present technology provides systems and methods that generate multiple anatomical models of the patient. For example, a first model may show the patient's native (e.g., pre-operative) anatomical configuration, and a second model may provide a simulation of the patient's corrected (e.g., post-operative) anatomical configuration. The second virtual model may optionally include one or more virtual implants shown as implanted at one or more target regions of the patient. Spine metrics (e.g., lumbar lordosis, Cobb angles, coronal parameters, sagittal parameters, pelvic parameters, etc.) can also be provided for both the pre-operative anatomical configuration and expected post-operative anatomical configuration. In some embodiments, the first and/or second virtual models can be used to perform one or more tests or simulations, for example, to determine a probability of one or more post-operative conditions (e.g., implant subsidence).

In some embodiments, the present technology includes generating, designing, and/or providing patient-specific medical procedures for multiple locations within a patient. For example, the present technology can include identifying at least two target regions or sites within a patient (e.g., a first vertebral level and a second vertebral level) for surgical intervention. The present technology can then design at least two patient-specific implants for implantation at the at least two target regions. The at least two patient-specific implants can each be specifically designed for their respective target region, and thus can have different geometries. In some embodiments, the corrected anatomical configuration of the patient is only achieved by implanting each of the at least two patient-specific implants. In the context of spinal surgery, for example, the present technology may provide a first patient-specific interbody device to be implanted between the L2 and L3 vertebrae, a second patient-specific interbody device to be implanted between the L3 and L4 vertebrae, and a third patient-specific interbody device to be implanted between the L4 and L5 vertebrae. In some embodiments, the present technology can include predicting a probability of one or more post-operative conditions (e.g., subsidence) for the at least two patient-specific implants, and/or designing the at least two patient-specific implants based on one or more subsidence-reducing parameters.

In some embodiments, the present technology can predict, model, and/or simulate disease progression within a particular patient to aid in diagnosis and/or treatment planning. The simulation can be done to model and/or estimate future anatomical configurations and/or spine metrics of the patient (a) if no surgical intervention occurs, or (b) for a variety of different surgical intervention options. The progression modeling can thus be used to determine the optimal time for surgical intervention and/or to select which surgical intervention provides the best long-term outcomes. In some embodiments, the disease progression modelling is performed using one or more machine learning models trained based on a plurality of reference patients. In some embodiments, the disease progression modeling can include using one or more predictive models and/or simulations to determine a probability of one or more post-operative events or conditions. For example, the disease progression modeling can include predicting a likelihood and/or magnitude of subsidence of one or more patient-specific implants. The predicted likelihood and/or magnitude of subsidence can aid in the treatment planning, for example, to determine and/or revise one or more aspects of a surgical intervention to at least partially reduce the likelihood of subsidence.

In a particular non-limiting example, the present technology includes a method for providing patient-specific medical care for a subject patient. The method can include receiving a patient-data set for the subject patient that includes one or more images of the patient's spinal region showing the patient's native anatomical configuration. The method can further include determining a corrected anatomical configuration for the subject patient that is different than the native anatomical configuration, and creating a virtual model of the corrected anatomical configuration. The method can further include generating surgical plan and designing one or more patient-specific implants for achieving the corrected anatomical configuration in the subject patient. In some embodiments, the corrected anatomical configuration and/or the one or more patient-specific implants can be associated with a reduced probability of one or more post-operative conditions (e.g., subsidence of the one or more patient-specific implants). In representative embodiments, the foregoing method can be performed by a system storing computer-executable instructions that, when executed, cause the system to perform the steps of method.

In a particular non-limiting example, the present technology includes a method for designing a patient-specific orthopedic implant for a subject patient. The method can include receiving a patient data set of the subject patient, the patient data set including spinal pathology data for the subject patient. The patient data set can be compared to a plurality of reference patient data sets to identify one or more similar patient data sets in the plurality of reference patient data sets, with each identified similar patient data set corresponding to a reference patient having similar spinal pathology to the subject patient and who received treatment with an orthopedic implant. The method can further include selecting a subset of the one or more similar patient data sets based on whether the similar patient data sets indicated the reference patient had a favorable outcome (e.g., a favorable orthopedic implant subsidence outcome) following implantation of their orthopedic implant. The method can further include identifying, for at least one similar reference patients of the selected subset, surgical procedure data and design data for the respective orthopedic implant that produced the favorable outcome in the similar reference patient. Based on the design data and the surgical produced data that produced the favorable outcome in the similar reference patient, the patient-specific orthopedic implant for the subject patient and a surgical procedure for implanting the patient-specific orthopedic implant into the subject patient can be designed. In some embodiments, the method can further include outputting fabrication instructions for causing a manufacturing system to manufacture the patient-specific orthopedic implant according to the generated design. In representative embodiments, the foregoing method can be performed by a system storing computer-executable instructions that, when executed, cause the system to perform the steps of method.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

B. Systems and Methods of Designing Patient-Specific Treatment Plans and Patient-Specific Medical Devices FIG. 1 is a network connection diagram illustrating a computing system 100 for providing patient-specific medical care, according to an embodiment. As described in further detail herein, the system 100 is configured to generate a medical treatment plan for a patient. In some embodiments, the system 100 is configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The medical treatment plan can include surgical information, surgical plans, technology recommendations (e.g., device and/or instrument recommendations), and/or medical device designs. For example, the medical treatment plan can include at least one treatment procedure (e.g., a surgical procedure or intervention) and/or at least one medical device (e.g., an implanted medical device (also referred to herein as an "implant" or "implanted device") or implant delivery instrument).

In some embodiments, the system 100 generates a medical treatment plan that is customized for a particular patient or group of patients, also referred to herein as a "patient-specific" or "personalized" treatment plan. The patient-specific treatment plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. As a specific example, and as described in greater detail with reference to FIGS. 5A-10, the patient-specific medical device can be designed based at least partially on one or more patient-specific subsidence parameters. However, it shall be appreciated that a patient-specific treatment plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice-versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications (e.g., implant subsidence), recovery times, efficacy, mortality, and/or follow-up surgeries.

In some embodiments, the server 106 receives at least some of the reference patient data sets from a plurality of healthcare provider computing systems (e.g., systems 112a-112c, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114a-114c, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted probability of implant subsidence, predicted magnitude of implant subsidence, predicted mortality, predicted related follow-up surgeries, or the like. In some embodiments, the server 106 can continuously or periodically analyze patient data (including patient data obtained during the patient stay) to determine near real-time or real-time risk scores, subsidence prediction(s), mortality prediction, etc.

In some embodiments, the server 106 includes one or more modules for performing one or more steps of the patient-specific treatment planning methods described herein. For example, in the depicted embodiment, the server 106 includes a data analysis module 116 and a treatment planning module 118. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, treatment levels, bone mass density, vertebral endplate strength, vertebra stiffness and/or any other suitable parameter. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications (e.g., implant subsidence), recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one treatment plan (e.g., pre-operative plans, surgical plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes (e.g., reduced probability of subsidence, reduced magnitude of subsidence, etc.) for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size (e.g., length, width, height, etc.), shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, strength and/or effective stiffness (e.g., lattice density, number of struts, location of struts, etc.). Effective stiffness can be described as the stiffness of the implant as designed. In some embodiments, the generated patient-specific medical device design is a design for an entire device. Alternatively, the generated design can be for one or more components of a device, rather than the entire device. In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 118 can also store various types of implant surgery information, such as implant parameters (e.g., types, dimensions, area of contact regions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the treatment plan(s). For example, the display 122 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 122 can show a design for a medical device to be implanted in the patient, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, the medical device design(s) generated by the treatment planning module 118 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the treatment plan, treatment progress can be monitored over one or more time periods to update the data analysis module 116 and/or treatment planning module 118. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110 the data analysis module 116, and/or the treatment planning module 118 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
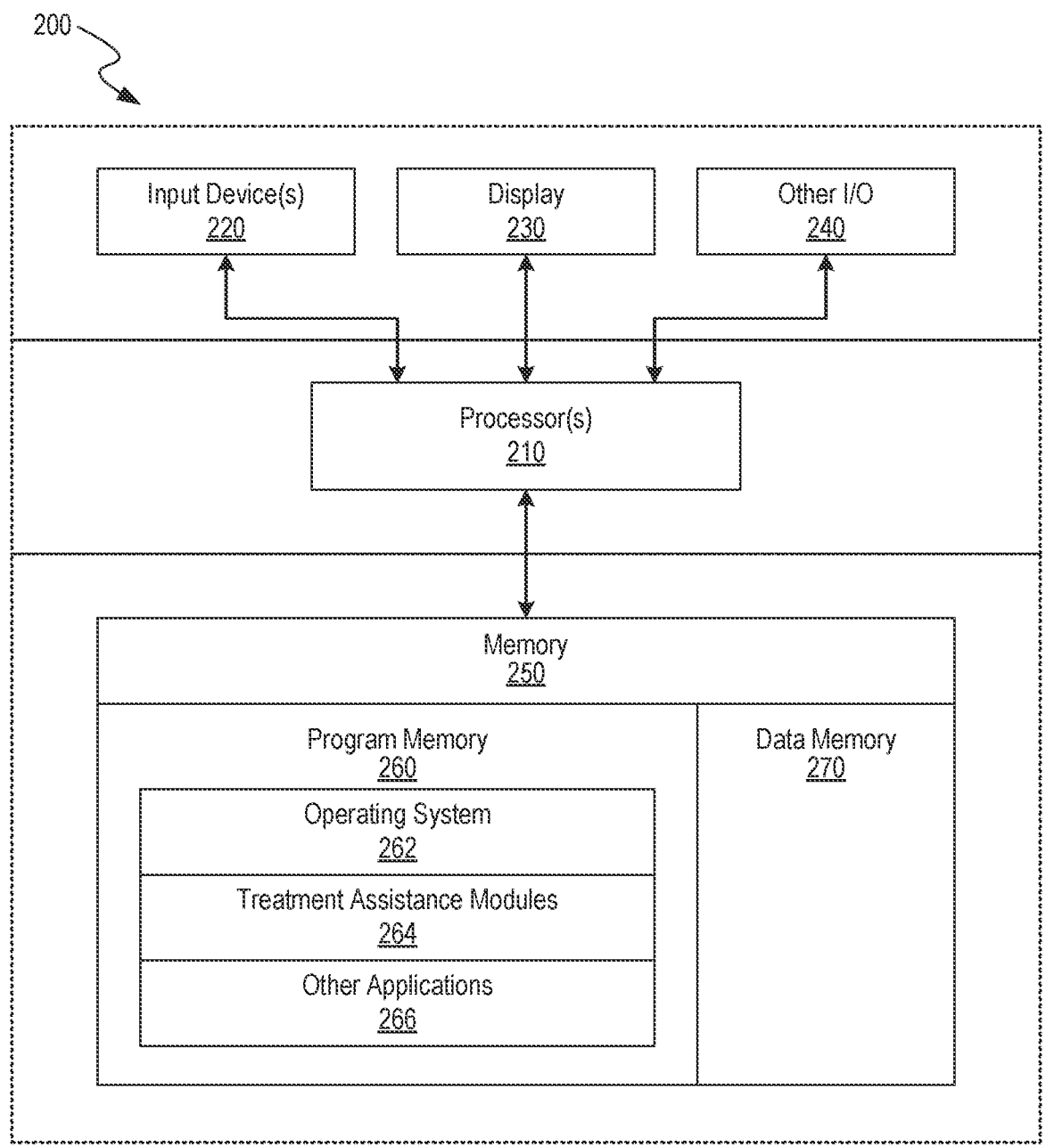
FIG. 2 illustrates a computing device suitable for use in connection with the system of FIG. 1, according to an embodiment.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
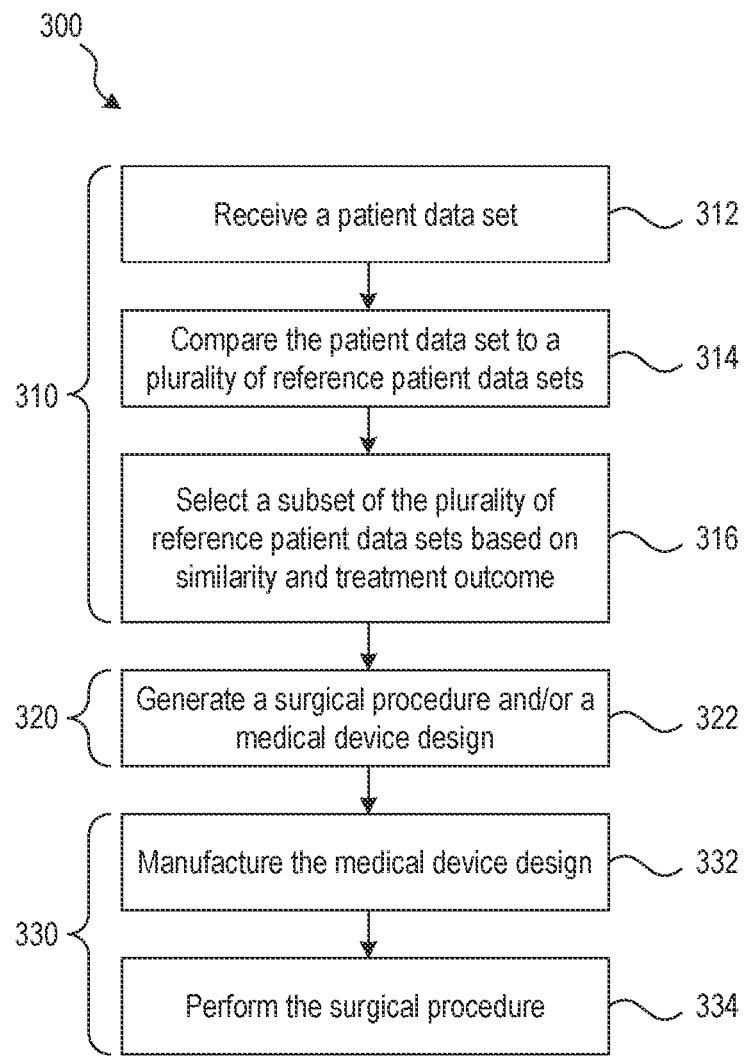
FIG. 3 is a flow diagram illustrating a method for providing patient-specific medical care, according to an embodiment.

FIG. 3 is a flow diagram illustrating a method 300 for providing patient-specific medical care, according to an embodiment. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, segment flexibility, bone quality, rotational displacement, or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications (e.g., implant subsidence). In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually, by a surgical robot, or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

Figure 4A:
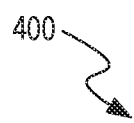

FIGS. 4A-4C illustrate exemplary data sets that may be used and/or generated in connection with the methods described herein (e.g., the data analysis phase 310 described with respect to FIG. 3), according to an embodiment. FIG. 4A illustrates a patient data set 400 of a patient to be treated. The patient data set 400 can include a patient ID and a plurality of pre-operative patient metrics (e.g., age, gender, BMI, lumbar lordosis (LL), pelvic incidence (PI), and treatment levels of the spine (levels)). FIG. 4B illustrates a plurality of reference patient data sets 410. In the depicted embodiment, the reference patient data sets 410 include a first subset 412 from a study group (Study Group X), a second subset 414 from a practice database (Practice Y), and a third subset 416 from an academic group (University Z). In alternative embodiments, the reference patient data sets 410 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 4C illustrates comparison of the patient data set 400 to the reference patient data sets 410. As previously described, the patient data set 400 can be compared to the reference patient data sets 410 to identify one or more similar patient data sets from the reference patient data sets. In some embodiments, the patient metrics from the reference patient data sets 410 are converted to numeric values and compared the patient metrics from the patient data set 400 to calculate a similarity score 420 ("Pre-op Similarity") for each reference patient data set. Reference patient data sets having a similarity score below a threshold value can be considered to be similar to the patient data set 400. For example, in the depicted embodiment, reference patient data set 410a has a similarity score of 9, reference patient data set 410b has a similarity score of 2, reference patient data set 410c has a similarity score of 5, and reference patient data set 410d has a similarity score of 8. Because each of these scores are below the threshold value of 10, reference patient data sets 410a-d are identified as being similar patient data sets.

The treatment outcome data of the similar patient data sets 410a-d can be analyzed to determine surgical procedures and/or implant designs with the highest probabilities of success. For example, the treatment outcome data for each reference patient data set can be converted to a numerical outcome score 430 ("Outcome Quotient") representing the likelihood of a favorable outcome. In the depicted embodiment, reference patient data set 410a has an outcome score of 1, reference patient data set 410b has an outcome score of 1, reference patient data set 410c has an outcome score of 9, and reference patient data set 410d has an outcome score of 2. In embodiments where a lower outcome score correlates to a higher likelihood of a favorable outcome, reference patient data sets 410a, 410b, and 410d can be selected. The treatment procedure data from the selected reference patient data sets 410a, 410b, and 410d can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof.

In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

C. Select Systems and Methods for Designing Implants with Reduced Subsidence

Figure 5A:
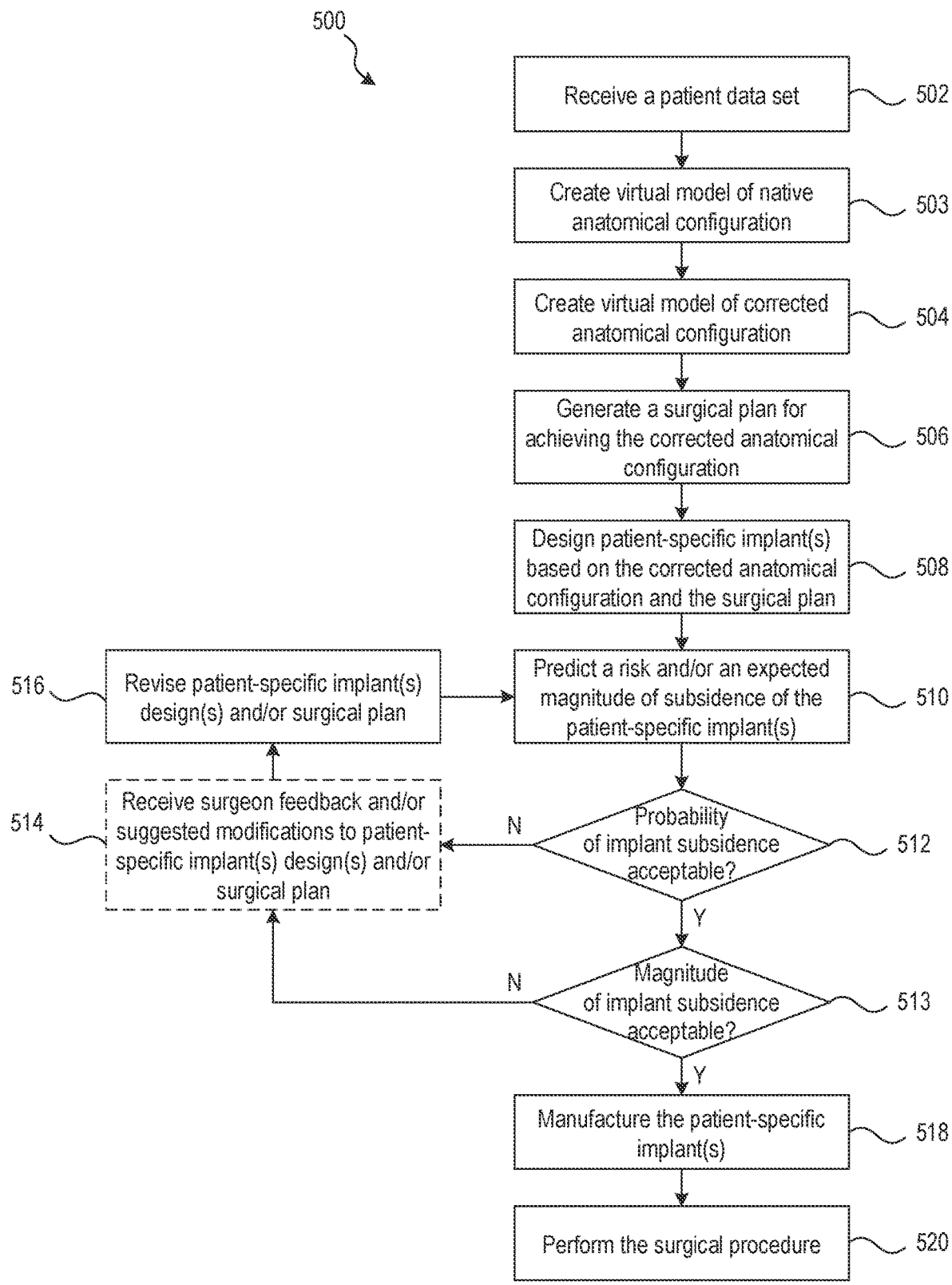
FIG. 5A is a flow diagram illustrating a method for designing a patient-specific treatment plan and one or more patient-specific implants having a reduced risk of post-surgical subsidence, according to an embodiment.

FIG. 5A is a flow diagram illustrating a method 500 for designing a patient-specific treatment plan and one or more patient-specific implants having a reduced risk of post-surgical subsidence, according embodiments of the present technology. The method 500 can begin in step 502 by receiving a patient data set for a particular patient in need of medical treatment. The patient data set can include data representative of the patient's condition, anatomy, pathology, symptoms, medical history, preferences, and/or any other information or parameters relevant to the patient. For example, the patient data set can include surgical intervention data, treatment outcome data (e.g., spinal pathology data, subsidence outcome data, etc.), progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1 or the computing system 606 described below with respect to FIG. 6. In some embodiments, the computing system that receives the patient data set in step 502 also stores one or more software modules (e.g., the data analysis module 116 and/or the treatment planning module 118, shown in FIG. 1, or additional software modules for performing various operations of the method 500).

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a two- or three-dimensional visual representation of the patient's native anatomy. The virtual model can be a 2D model, 3D model, and/or computer-generated CAD model constructed by, for example, converting image data into features (e.g., 2D data, volumetric data containing voxels, surface data, etc.) that are representative of anatomy based on segmentation, volumetric presentations, and/or feature extraction. In some embodiments, one or more segmentation processes can be used to separate voxels representing different anatomical elements, such as bony anatomy from the other anatomy. For example, isolation of individual bony structures enables a user to manipulate each bony structure independently. The relationships (distances, angles, constraints, etc.) between individual bony structures (e.g., vertebrae) or other modeled features can be analyzed and adjusted. In some embodiments, volume representations can be generated based on surface-based volume rendering and voxel representations. The techniques for generating virtual models can be selected based on the available patient data, desired model analytics, and/or desired virtual model modifications. Additionally, the modeling techniques described herein may, in certain embodiments, be used in connection with or incorporate one or more of the modeling techniques or steps disclosed in U.S. application Ser. No. 16/569,494, filed on Sep. 12, 2019, titled "SYSTEMS AND METHODS FOR ORTHOPEDIC IMPLANTS," which is incorporated by reference in its entirety.

The virtual model can include, without limitation, modeling data, material properties (e.g., yield strength, elastic modulus, fracture toughness, etc.), parametric modeling parameters (e.g., constraints, features, dimensions, etc.), direct modeling parameters, mesh parameters (e.g., node data, finite element analysis (FEA) mesh, boundary conditions, etc.), surface modeling parameters (e.g., data for generating surfaces, topology, etc.), extracted features, or the like. In some embodiments, CAD software is used to generate a virtual model using parametric modeling techniques and can select, modify, and set constraints between features or components. The constraints can be adjusted to set lordosis, Cobb angles, coronal parameters (e.g., coronal balance, global coronal balance, coronal pelvic tilt, etc.), sagittal parameters (e.g., pelvic incidence, pelvic tilt, sacral slope, thoracic kyphosis, etc.), pelvic parameters, and/or other parameters disclosed herein. The CAD software can be used to, for example, individually or collectively move anatomic features (e.g., modeled vertebrae, modeled implants, etc.), modify anatomic features, simulate motion, or the like.

The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected anatomical configuration (which can also be referred to herein as the "planned configuration," "optimized geometry," "post-operative anatomical configuration," or "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4C (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, and/or a target intervertebral space height. The difference between the native anatomical configuration and the corrected anatomical configuration may be referred to as a "patient-specific correction" or "target correction."

Once the corrected anatomical configuration is determined, the computing system can generate a two- or three-dimensional visual representation of the patient's anatomy with the corrected anatomical configuration. As with the virtual model created in step 503, the virtual model of the patient's corrected anatomical configuration can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region in a corrected anatomical configuration, including some or all of the sacrum, lumbar region, thoracic region, and/or cervical region. In some embodiments, the virtual model includes soft tissue, cartilage, and other non-bony structures. In other embodiments, the virtual model only includes the patient's bony structures.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, etc.) across a specific range of vertebral levels (e.g., L1-L4, L1-5, L3-T12, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, coronal parameters, sagittal parameters, and/or pelvic parameters) corresponding to the expected post-operative patient anatomy. The surgical plan can be generated by the same or different computing system that created the virtual model of the corrected anatomical configuration. In some embodiments, the surgical plan can also be based on one or more reference patient data sets as previously described with respect to FIGS. 1-4C. In some embodiments, the surgical plan can also be based at least in part on surgeon-specific preferences and/or outcomes associated with a specific surgeon performing the surgery. In some embodiments, more than one surgical plan is generated in step 506 to provide a surgeon with multiple options.

The method 500 can continue in step 508 by designing (e.g., via the same computing system that performed steps 502-506) a patient-specific implant based on the corrected anatomical configuration and the surgical plan. For example, the patient-specific implant can be specifically designed such that, when it is implanted in the particular patient, it directs the patient's anatomy to occupy the corrected anatomical configuration (e.g., transforming the patient's anatomy from the native anatomical configuration to the corrected anatomical configuration). The patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific implant is designed solely based on the virtual model of the corrected anatomical configuration and/or without reference to pre-operative patient images.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.).

In some embodiments, designing the implant in step 508 can optionally include generating fabrication instructions for manufacturing the implant. For example, the computing system may generate computer-executable fabrication instructions that that, when executed by a manufacturing system, cause the manufacturing system to manufacture the implant.

The method 500 can continue in step 510 by predicting (e.g., via the same computing system that performed steps 502-508) a risk of subsidence, and/or an expected magnitude of subsidence, of the patient specific implant(s) designed in step 508. In some embodiments, step 510 includes predicting one or more additional properties associated with the probability and/or magnitude of subsidence, such as a type of subsidence and/or a subsidence onset time.

The probability and/or magnitude of subsidence can be predicted using one or more predictive model(s) that can be generally similar to or the same as the predictive model(s) described previously and with reference to FIGS. 1-4C. For example, the predictive model(s) may analyze reference patient data sets for a plurality of patients who received a similar surgical intervention and/or had similar pathology and mechanical properties. The data used by the predictive model(s) can include the patient data set of step 502, the native virtual model of step 503, the corrected virtual model of step 504, the surgical plan of step 506, the design(s) for the patient-specific implant(s) of step 508, one or more reference patient data sets (e.g., the reference patient data sets 114 of FIG. 1, the reference patient data sets 410 of FIG. 4B, etc.), and/or any other suitable data. In some embodiments, multiple predictive models are generated and/or used to analyze the same patient data set. For example, a spine correction predictive model can be generated using a patient data set. A subsidence predictive model can then be generated using a subset of the patient data set in which the subset has matching features for subsidence prediction. In some embodiments, multiple predictive models are generated and/or used to analyze different patient data sets. For example, a spine correction predictive model can be generated using a first patient data set of prior patients with similar corrections. A subsidence predictive model can be generated based on the spine correction predictive model using a second patient data set of prior patients with matching mechanical properties of anatomy or other subsidence related characteristics. The subsidence predictive modeling can include disk-height or implant subsidence models, vertebral body subsidence models, or the like.

As described in greater detail below regarding FIG. 5B, the predictive model(s) can predict the probability and/or expected magnitude of subsidence for each of the patient-specific implants based at least in part on (i) one or more mechanical properties (e.g., endplate stiffness, strength, hardness, elastic modulus, etc.) of at least one of the patient's vertebra, (ii) one or more predicted changes to at least one of the mechanical properties, (iii) predicted bony ingrowth between the patient-specific implant(s) and the at least one vertebra, and/or (iv) the design(s) of the patient-specific implant(s).

In some embodiments, the predictive model(s) can be configured to predict the probability and/or magnitude of subsidence for a particular patient over one or more time periods and/or at one or more times after surgical intervention. For example, subsidence can be most likely to occur within three months after the patient-specific implant(s) are implanted. Accordingly, in some embodiments the predictive model(s) can be configured to predict the probability and/or magnitude of subsidence between about 1 day and about 6 months after surgical intervention, such as up to 1 week, 2 weeks, 3 weeks, 1 month, 2 months, 3 months, and/or any other suitable time period after surgical intervention. In some embodiments, the predictive model(s) can be configured to predict the probability and/or magnitude of subsidence over at least 1 year, 2 years, 3 years, 4 years, or over any other suitable time period after surgical intervention. In at least some embodiments, the predictive model(s) can be configured to predict the probability and/or magnitude of subsidence over an expected lifetime of the patient-specific implant(s). In some embodiments, step 510 can optionally include predicting rates of subsidence based on, for example, post-surgery plans (e.g., post-surgery therapy, patient activity, etc.), bone ingrowth, ancillary procedures (e.g., fusion procedures, such rod system fusions), or the like. Predicting the rate, probability and/or magnitude of subsidence over one or more time periods and/or at one or more times after surgical intervention can be generally similar to or the same as modelling the progression of a disease (e.g., a spinal disease or condition) over time. Disease progression modelling is described in greater in PCT Application No. PCT/US21/12065, filed Jan. 4, 2021, titled "PATIENT-SPECIFIC MEDICAL PROCEDURES AND DEVICES, AND ASSOCIATED SYSTEMS AND METHODS," the entirety of which is incorporated by reference herein in its entirety.

In some embodiments, step 510 includes predicting the probability of one or more subsidence outcomes. For example, the predictive model may, based on its analysis of the mechanical properties of patient anatomy and the implant design, determine (1) the probability of having no post-surgical subsidence, and (2) the probability of having subsidence of various magnitudes. As a particular non-limiting example, the predictive model may determine that a given patient has a 60% likelihood of having no subsidence, a 30% likelihood of having subsidence of between 0.1 mm and 2 mm, and a 10% change of having subsidence greater than 2 mm.

The method 500 can continue in step 512 by determining whether the probability of subsidence (e.g., step 510) of the patient-specific implant(s) (e.g., step 508) is acceptable. This may include, for example, comparing the probability of subsidence to a predetermined threshold or rule. In some embodiments, the probability of subsidence is measured as a percent likelihood of the patient experiencing post-surgical subsidence, and the predetermined threshold is an upper bound of an acceptable likelihood of subsidence, such as 5%, 10%, 15%, 20%, 30%, or the like. If the probability of subsidence is less than the predetermined threshold (e.g., if the predetermined threshold is 10% and the probability of subsidence is 5%), the method 500 can continue to step 518 as described below. If the probability of subsidence is greater than the predetermined threshold (e.g., if the predetermined threshold is 10% and the probability of subsidence is 15%), the method 500 can continue to step 516 described below. In some embodiments, the predetermined threshold can be based at least in part on a general or reference probability of implant subsidence. The general probability of implant subsidence can be, for example, the percent of reference patients (e.g., all or a subset of reference patients) that experienced implant subsidence. In such embodiments, the predetermined threshold can be between about 0.1% and about 90% less than the general probability of implant subsidence, such as at least 1%, 5%, 10%, 20%, 25%, 50%, or any other suitable percent less than the general probability. In some embodiments, determining whether the probability of predicted subsidence is acceptable can include receiving user (e.g., surgeon) feedback in addition to or in lieu of comparing the predicted subsidence probability to the predetermined threshold.

In addition to or in lieu of determining whether the probability of subsidence is acceptable, the method 500 can optionally continue in step 513 by determining whether the magnitude of predicted subsidence (e.g., step 510) of the patient is acceptable. This may include, for example, comparing the predicted magnitude of subsidence to a predetermined threshold or rule. In some embodiments, the predicted magnitude of subsidence is measured in distance (e.g., mm), and the predetermined threshold or rule is an upper bound of an acceptable subsidence distance, such as 1 mm, 2 mm, 3 mm, 4 mm, 5 mm, or the like. If the predicted magnitude of subsidence is less than the predetermined threshold (e.g., if the predetermined threshold is 2 mm and the predicted subsidence is 1 mm), the method 500 can continue in step 518 as described below. If the predicted magnitude of subsidence is greater than the predetermined threshold (e.g., if the predetermined threshold is 2 mm and the predicted subsidence is 3 mm), the method 500 can continue in step 516 as described below. In some embodiments, the predetermined threshold can be an adaptive patient-specific threshold determined by analyzing a plurality of reference-patient data sets and determining, for the particular patient, how much subsidence would be acceptable while still maintaining a positive surgical outcome. In some embodiments, determining whether the magnitude of predicted subsidence is acceptable can include receiving user (e.g., surgeon) feedback in addition to or in lieu of comparing the predicted subsidence magnitude to the predetermined threshold.

In at least some embodiments, the method 500 can optionally continue in step 514 by receiving surgeon feedback and/or suggested modifications to the design(s) of the patient-specific implant(s) (e.g., step 508) and/or the surgical plan (e.g., step 506). The surgeon can review the patient-specific implant design(s) and/or surgical plan and the associated predicted probability and/or magnitude of subsidence and, in step 514, either approve or reject the patient-specific implant design(s) and/or the surgical plan (or, if more than one surgical plan is provided in step 508, the surgeon can select one of the provided surgical plans). If the surgeon does not approve the probability or magnitude of implant subsidence, and/or if the probability or magnitude of implant subsidence does not meet the predetermined threshold, the surgeon can optionally provide feedback and/or suggested modifications to the surgical plan (e.g., by adjusting the virtual model or changing one or more aspects about the plan) and/or the patient-specific implant(s) (e.g., by adjusting one or more aspects of the design(s)). Accordingly, the method 500 can include receiving (e.g., via the computing system) the surgeon feedback and/or suggested modifications. If surgeon feedback and/or suggested modifications are received in step 514, the method 500 can continue in step 516 by revising (e.g., automatically revising via the computing system) the virtual model and/or surgical plan based at least in part on the surgeon feedback and/or suggested modifications received in step 514. Additionally, or alternatively, the surgeon can review, modify, approve, and/or reject the corrected anatomical configuration shown via the virtual model. Revising the virtual model(s) can include, for example, generating a revised corrected anatomical configuration.

If the probability of implant subsidence is determined to not be acceptable in step 512, the method 500 continues in step 516 by revising the patient-specific implant design and/or the surgical plan to reduce the probability and/or magnitude of predicted subsidence. This can include, for example, adjusting (e.g., automatically adjusting) (1) the surgical plan based on surgical plan parameters associated with a reduced probability of (or expected magnitude of) subsidence, and/or (2) the implant design based on implant design parameters associated with a reduced probability of (or expected magnitude of) subsidence.

The surgical plan parameter(s) associated with a reduced likelihood of subsidence and/or a reduced magnitude of predicted subsidence can include:

Reducing and/or minimizing removal of one or more vertebral endplates during the surgical procedure to reduce or minimize the loss of bone strength of the associated vertebra and/or vertebral bone;

If vertebral endplate removal is necessary (e.g., to promote vascular/bone ingrowth to the graft), removing only a small portion from the center or center portion of the vertebral endplate;

Reducing the number of holes (e.g., graft holes, bore holes, anchoring holes, etc.) created in vertebral bone and/or combining one or more holes, e.g., to at least partially reduce the surface area exposed to fracture stresses;

Identifying one or more generally or substantially rectangular and/or rectangular-shaped areas or regions of a vertebral endplate to contact and/or support the patient-specific implant(s);

Improving a segmental lumbar lordosis correction in the virtual model and/or the corrected anatomical configuration;

Increasing an amount of bone graft (e.g., increased cross-sectional area and/or height);

Improving fitting of bone graft to vertebral body(ies) and/or endplate(s) in target region;

Improving target region preparation, including removing all or part of the cartilaginous endplate;

Using supplemental implant fixation (e.g., bilateral pedicle screws, posterior fixation, ventral plate, etc.);

Increasing an amount of filling material (e.g., bone cement, etc.) provided along with the patient-specific implant(s); and/or Any other suitable surgical plan parameter(s), including changing an implant delivery path, changing one or more of the target regions (e.g., positions of the implant), etc.

For a given one or more target regions in a patient's spine, the implant design parameter(s) associated with a reduced likelihood of subsidence and/or a reduced magnitude of predicted subsidence can include:

Increasing (e.g., maximizing) implant contact (e.g., contact surface area) with a periphery of the vertebral bodies (e.g., with cortical bone and/or the apophyseal ring);

Reducing (e.g., minimizing) alignment of load-bearing portion(s) of the implant (e.g., the edges, protrusions/patient-specific topologies, etc.) with the center or center region(s) (e.g., cancellous bone) of the vertebral bodies;

Increasing (e.g., maximizing) alignment of load-bearing portion(s) of the implant with portions of the vertebral body having increased stiffness;

Increasing (e.g., maximizing) implant contact (e.g., contact surface area) with a posterior portion of the vertebral body (e.g., posterolateral position(s), etc.) and/or reducing (e.g., minimizing) implant contact with an anterior portion of the vertebral bodies;

Increasing (e.g., maximizing) a ratio of implant contact surface area to endplate surface area, for example, to be at least 65% (e.g., implant contacts at least 65% of vertebral endplate);

Optimizing (e.g., maximizing, aligning) implant strength and/or stiffness;

Manufacturing the implant at least partially from Polyether ether ketone (PEEK);

Increasing a width (e.g., measured laterally relative to vertebral and/or spine) of the patient-specific implant(s) and/or increasing contact with one or more lateral portions of the vertebral bodies;

Improving fitting of the patient-specific implants to a respective target region of a vertebral bodies and/or endplates;

For patient-specific implant(s) that are not at least partially supported by the apophyseal ring, reducing length (e.g., measured anterior-to-posterior) of the patient-specific implant(s);

Reducing (e.g., minimizing) motion the patient-specific implant(s) relative to the endplate(s), for example, by improving fitting of the patient-specific implant(s), matching an implant surface topography with a topography of the corresponding endplate(s), increasing a contact area ratio (as described previously), etc.;

Increasing an amount of bone graft (e.g., increased cross-sectional area and/or height);

Improving fitting of bone graft to vertebral body(ies) and/or endplate(s) in target region; and/or Any other suitable design parameter(s) associated with a reduced likelihood of subsidence and/or a reduced magnitude of predicted subsidence.

In some embodiments, revising the design(s) for the patient-specific implant(s) includes revising one or more portions or aspects of the design(s). In at least some embodiments, revising the design(s) can include revising an entire design of one or more of the patient-specific implants. In some embodiments, the design(s) can be revised in response to one or more revisions to the surgical plan. Likewise, in some embodiments the surgical plan can be revised based at least partially on one or more revisions to the design(s) for the patient-specific implant(s).

In some embodiment, use of one or more secondary implants can reduce the probability of and/or predicted magnitude of subsidence, in addition to, or in lieu of, adjusting the surgical plan parameters and/or adjusting the implant design characteristics. For example, a spinal support system (e.g., a rod, a plate, etc.) can be implanted in combination with the interbody implant (or interbody implants at the same or different levels) to provide additional stability and anti-subsidence support to the interbody implant. In embodiments in which the surgical plan already calls for secondary implants (e.g., rods, plates, etc.) in addition to the interbody implant, the number of or characteristics of the secondary implants can be changed to reduce the probability of and/or predicted magnitude of subsidence.

For example, if predicted subsidence exceeds a predetermined threshold, the surgical plan can be revised to include one or more extra secondary implants and/or to stiffen the one or more secondary implants to provide anti-subsidence support.

In some embodiments, the surgical plan parameter(s) and/or implant design parameter(s) to be adjusted can be provided and/or selected by a user (e.g., the surgeon), and/or can be automatically selected by the predictive model(s)/computing system. In some embodiments, the surgical plan parameter(s) can be based at least partially on the patient data of step 502, the reference patient data set(s), and/or the predicted probability and/or magnitude of subsidence in step 510 (e.g., the predicted change in mechanical properties, the predicted bony ingrowth, etc.).

In some embodiments, revising the design(s) of the patient-specific implant(s) and/or surgical plan in step 516 can further include revising the design(s) in response to the presence of one or more patient-specific parameters or factors associated with an increased probability and/or predicted magnitude of subsidence. The patient-specific parameter(s) can be determined from and/or based at least partially on the patient data of step 502. The patient-specific parameter(s) can include:

Patient physical activity, including non-compliance with postoperative regimens;
Patient weight and/or BMI (e.g., patient obesity);
Patient use of cigarette and/or other tobacco or otherwise harmful products or substances;
Use and/or frequency of use of nonsteroidal anti-inflammatory agents;
Patient age and/or bone mass density; and/or
Any other suitable patient-specific parameter(s) associated with an increased probability and/or predicted magnitude of subsidence.

In some embodiments, one or more computing systems (e.g., the same computing system that performed steps 502-512) can optionally provide one or more recommended changes/adjustments to the surgical plan and/or implant design to decrease the probability of and/or predicted magnitude of subsidence. For example, the computing system may include one or more trained machine learning models or artificial intelligence architectures that can automatically analyze the proposed surgical plan and implant in combination with patient tissue characteristics to identify one or more parameters that can be adjusted to reduce the probability of and/or predicted magnitude of subsidence. In some embodiments, the system may identify one, two, three, four, or more surgical plan parameters and/or implant design parameters recited above that, for the particular surgical plan, implant, and patient, can be adjusted to reduce the probability of and/or expected magnitude of subsidence. For example, the system may, based on its analysis, determine that the appropriate parameters to manipulate include increasing an amount of bone cement used and increasing the surface area contact between the implant and the vertebral endplate. In another embodiment, the system may, based on its analysis, determine that the implant position should be adjusted. In yet another example, the system may determine that an additional secondary implant (e.g., rod) should be implanted to provide anti-subsidence support. The foregoing are provided by way of example only, and one skilled in the art will appreciate that, depending on the particular patient and surgical plan, the system may recommend other adjustments to the surgical plan and/or implant to achieve a desired reduction in probability of and/or predicted magnitude of subsidence.

In some embodiments, the system may identify more than one change (or more than one combination of changes) that can be made to the surgical plan and/or implant to achieve a particular desired reduction in probability of and/or predicted magnitude of subsidence to comply with one or more predetermined thresholds. In such embodiments, the system may rank the changes (or combinations of change) based on, for example, degree of reduction in probability of and/or predicted magnitude of subsidence (e.g., if a first set of changes reduces the probability of subsidence to a greater degree than a second set of changes, the first set would be ranked higher than the second set), ease of implementing the change(s), impact on other surgical outcome parameters (e.g., recovery time, patient pain, mobility, range of motion, etc.), or a combination thereof. A user can then review the ranked list of proposed changes (or combination of changes) and select which change (or combination of changes) to implement.

One or more of the steps 510, 512, 513, 514, and 516 can be repeated as many times as necessary until the probability and/or predicted magnitude of subsidence is acceptable (e.g., as determined in steps 512 and 513, respectively). For example, the surgical plan parameter(s) and/or implant design parameter(s) can be iteratively modified to perform additional simulations to provide output for providing rates of subsidence and modifications for keeping the rates of subsidence or magnitude of subsidence at or below an acceptable level, which can be selected by the physician, selected by systems based historical data, etc. The method 500 can include performing single level or multi-level analysis to generate candidate surgical plan parameter(s) and/or implant design parameter(s) (e.g., for physician review).

In some embodiments, one or more of the steps 510-516 can be performed as part of designing the patient-specific implant(s) in step 508. For example, in at least some embodiments designing the patient-specific implant(s) can include predicting a probability of subsidence of the patient-specific implant(s) (e.g., step 510) and/or revising the design(s) for the patient-specific implant(s) based on one or more parameters associated with a reduced risk of subsidence (e.g., step 516).

If the probability and/or predicted magnitude of implant subsidence is determined as acceptable in steps 512 and/or 513, respectively, the method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1 or the manufacturing system 630 described below with respect to FIG. 6). In some embodiments, the implant is manufactured by the manufacturing system executing the computer-readable fabrication instructions generated by the computing system in step 508.

Once the implant is manufactured in step 518, the method 500 can continue in step 520 by implanting the patient-specific implant into the patient. The surgical procedure can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure. Additional details regarding a robotic surgical platform are described below with respect to FIG. 6.

The method 500 can be implemented and performed in various ways. In some embodiments, steps 502-516 can be performed by a computing system (e.g., the computing system 606 described below with respect to FIG. 6) associated with a first entity, step 518 can be performed by a manufacturing system associated with a second entity, and step 520 can be performed by a surgical provider, surgeon, and/or robotic surgical platform associated with a third entity. Any of the foregoing steps may also be implemented as computer-readable instructions stored in memory and executable by one or more processors of the associated computing system(s).

Figure 5B:
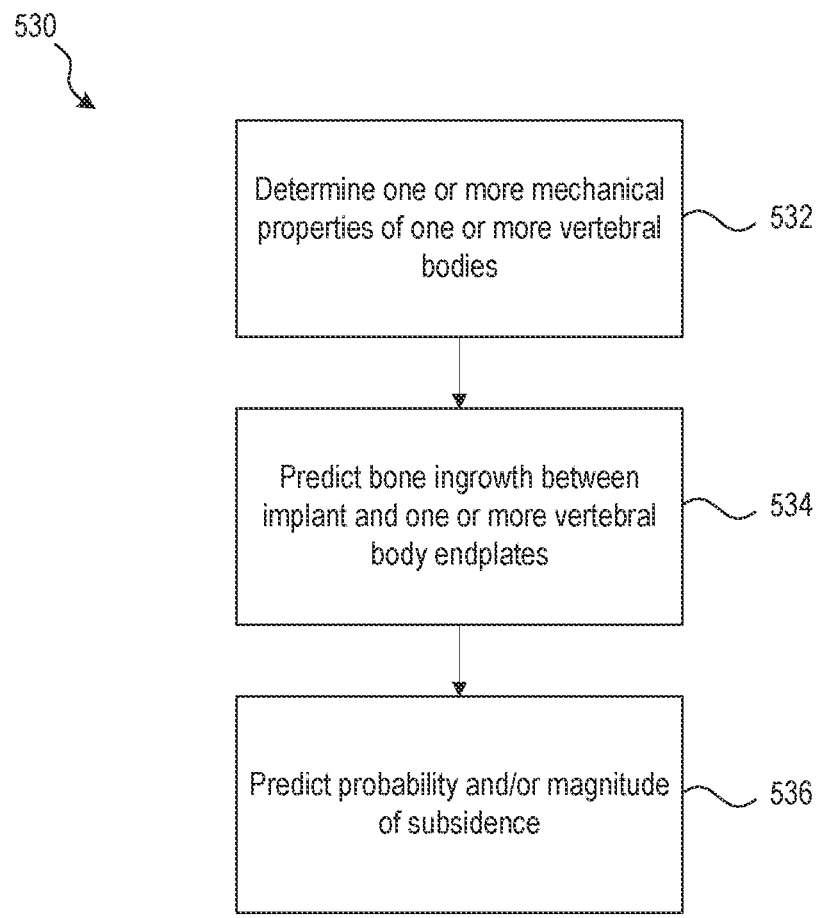
FIG. 5B is a flow diagram illustrating a method for predicting a probability of subsidence of one or more patient-specific implants, according to an embodiment.

FIG. 5B is a flow diagram illustrating a method 530 for predicting a probability of subsidence of one or more patient-specific implants, in accordance with embodiments of the present technology. The method 530 can be generally similar to or the same as step 510 of the method 500. Accordingly, in at least some embodiments, one or more steps of the method 530 can be a part of step 510 of the method 500 of FIG. 5A. Additionally, one or more steps of the method 530 can be performed by a computing system, program or model, including those previously described herein.

The method 530 can begin in step 532 by determining one or more mechanical properties of one or more vertebral bodies. The vertebral bodies can include vertebral bodies that will be contacted by an interbody implant to be implanted in accordance with a surgical plan, such as the surgical plan designed in step 506 of the method 500. In at least some embodiments, for example, the vertebral bodies can include a superior vertebral body and an inferior vertebral body that together define a target region (e.g., a target implantation region for a patient-specific implant) of a patient's spine. The mechanical properties can be determined based at least in part on the patient data set of step 502 (e.g., CT data, patient demographic data, etc.), the native virtual model of step 503, the corrected virtual model of step 504, the surgical plan of step 506, the design(s) for the patient-specific implant(s) of step 508, one or more reference patient data sets (e.g., the reference patient data sets 114 of FIG. 1, the reference patient data sets 410 of FIG. 4B, etc.), and/or any other suitable data. For example, in some embodiments step 532 can include determining a strength, stiffness, a hardness, and/or an elastic modulus of one or more endplates of the vertebral bodies before, during, and/or after surgical intervention. In some embodiments, step 532 includes determining the mechanical properties based at least in part on one or more bone density calibration tools, such as any suitable bone density calibration tool known to those of skill in the art. In some embodiments, step 532 includes performing one or more tests or simulations (e.g., spine orientation after implantation, simulated load sharing between one or more vertebral bodies, forces or loads with and without posterior fixation, forces or loads on implant and/or vertebral bodies based on patient weight, forces or loads on implant and/or one or more spine segments through daily activities, etc.) using simulated vertebral bodies and/or simulated spine segments based at least in part on the patient data. In some embodiments, step 532 includes using finite element analysis methods, statistical analysis and/or any other suitable model, process, or technique to determine the mechanical properties.

The method 530 can continue in step 534 by predicting bone ingrowth between a patient-specific implant and one or more vertebral body endplates. The endplate(s) can be at least partially contacting, proximate, and/or adjacent to the patient-specific implant when the patient-specific implant is implanted (e.g., in the target region). The predicted bone ingrowth can be based at least partially on a graft window size of the patient-specific implant, a porosity of the patient-specific implant, a porosity of the endplate(s), one or more forces or loads on the patient-specific implant, and/or one or more forces or loads on the endplate(s). In some embodiments, predicting bone ingrowth can include comparing the predicted bone ingrowth to existing and/or reference bone ingrowth data for patient-specific implants have a generally similar or a same porosity, using experimental and/or reference data (e.g., from one or more animal studies) to evaluate bone ingrowth over time, and/or using statistical analysis to revise and/or adjust the predicted bone ingrowth based on one or more aspects of the design(s) of the patient-specific implant(s). In some embodiments, predicting the bone ingrowth can include predicting a change (e.g., over a time period) to one or more of the mechanical properties of step 532 (e.g., a change in endplate stiffness over time, etc.).

The method 530 can continue in step 536 by predicting a probability and/or a magnitude of implant subsidence. The predicted probability and/or magnitude of implant subsidence can be based at least partially on the one or more mechanical properties of step 532, the one or more tests or simulations described previously and with reference to step 532, the predicted bone ingrowth and/or changes in the one or more mechanical properties of step 534, and/or one or more aspects of the design (e.g., size, implant location, graft size, strength, stiffness, etc.) of the patient-specific implant. In some embodiments, predicting the probability of subsidence can include modelling and/or simulating the interaction between the patient-specific implant and one or more vertebral bodies to evaluate a patient-specific implant design. For example, one or more simulated forces or loads (e.g., compressive loads, torsional loads, shear forces, etc.) can be applied to the patient-specific implant and/or the one or more vertebral bodies and, based on the response, the design for the patient-specific implant can be adjusted or revised based on one or more parameters associated with a reduced risk of subsidence (e.g., align load-bearing portion(s) of the patient specific implant with region(s) of the vertebral bodies having increased stiffness, strength, etc.). In some embodiments the predicted probability and/or magnitude of subsidence can be evaluated to determine whether the predicted probability and/or magnitude of subsidence is acceptable, such as described previously with reference to steps 512 and/or 513, respectively, of FIG. 5A.

Figure 6:
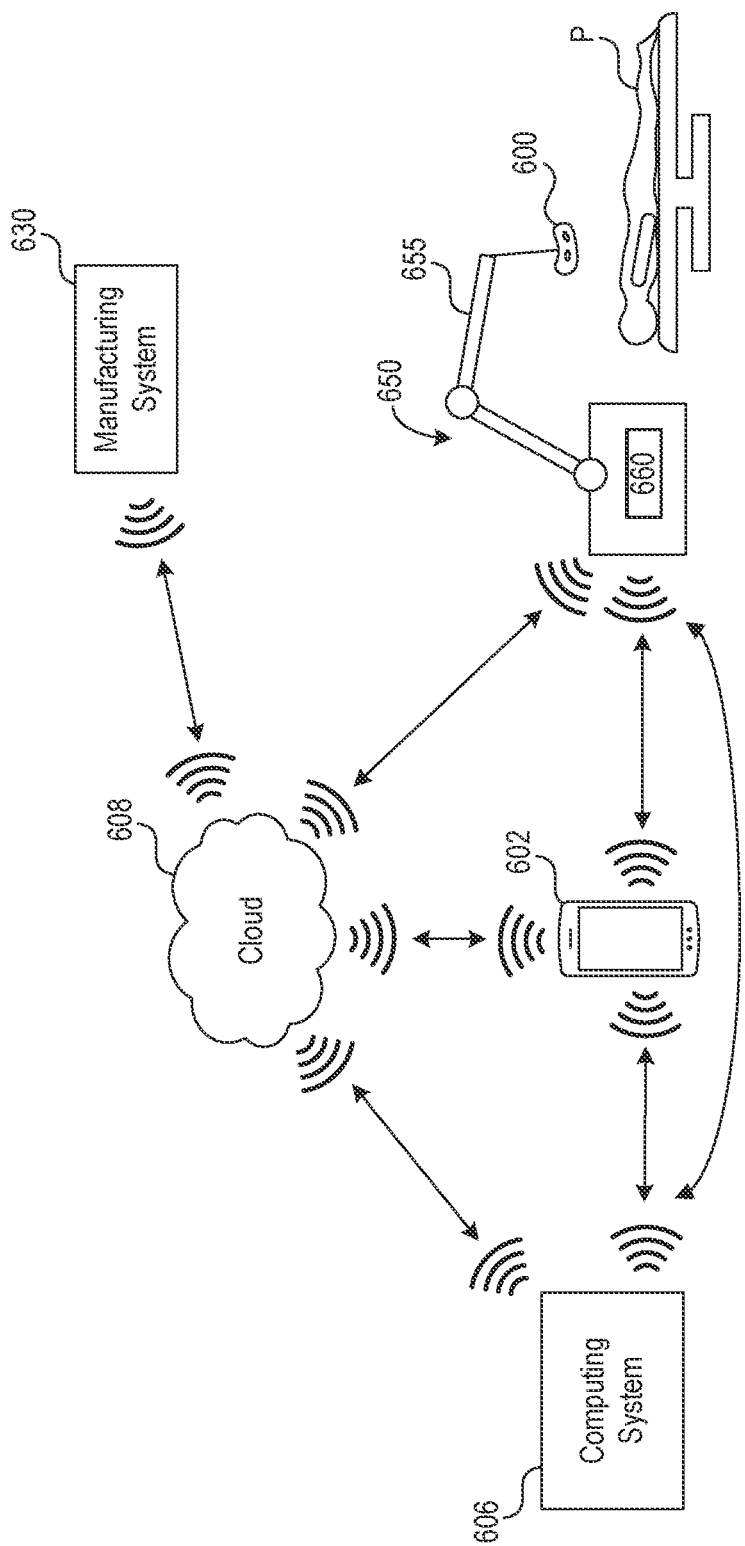
FIG. 6 is a partially schematic illustration of an operative setup and associated computing systems for providing patient-specific medical care, according to an embodiment.

FIG. 6 is a schematic illustration of an operative setup including select systems and devices that can be used to provide patient-specific medical care, such as for performing one or more steps of the method 500 and/or the method 530 described with respect to FIGS. 5A and 5B, respectively. As shown, the operative setup includes a computing device 602, a computing system 606, a cloud 608, a manufacturing system 630, and a robotic surgical platform 650. The computing device 602 can be a user device, such as a smart phone, mobile device, laptop, desktop, personal computer, tablet, phablet, or other such devices known in the art. In operation, a user (e.g., a surgeon) can collect, retrieve, review, modify, or otherwise interact with a patient data set using the computing device 602. The computing system 606 can include any suitable computing system configured to store one or more software modules for identifying reference patient data sets, determining patient-specific surgical plans, generating virtual models of patient anatomy, designing patient-specific implants, or the like. The one or more software modules can include algorithms, machine-learning models, artificial intelligence architectures, or the like for performing select operations. The cloud 608 can be any suitable network and/or storage system, and may include any combination of hardware and/or virtual computing resources. The manufacturing system 630 can be any suitable manufacturing system for producing patient-specific implants, including any of those previously described herein. The robotic surgical platform 650 (referred to herein as "the platform 650") can be configured to perform or otherwise assist with one or more aspects of a surgical procedure.

In a representative operation, the computing device 602, the computing system 606, the cloud 608, the manufacturing system 630, and the platform 650 can be used to provide patient-specific medical care, such as to perform one or more steps of the methods 500, 530 described previously with respect to FIGS. 5A and 5B. For example, the computing system 606 can receive a patient data set from the computing device 602 (e.g., step 502 of the method 500). In some embodiments, the computing device 602 can directly transmit the patient data set to the computing system 606. In other embodiments, the computing device 602 can upload the patient data set into the cloud 608, and the computing system 606 can download or otherwise access the patient data set from the cloud. Once the computing system 606 receives the patient data set, the computing system 606 can create a virtual model of the patient's native anatomical configuration (e.g., step 503 of the method 500), create a virtual model of the corrected anatomical configuration (e.g., step 504 of the method 500), and/or generate a surgical plan for achieving the corrected anatomical configuration (e.g., step 506 of the method 500). The computing system can perform the foregoing operations via the one or more software modules, which in some embodiments include machine learning models or other artificial intelligence architectures. Once the virtual models and the surgical plan are created, the computing system 606 can transmit the virtual models and the surgical plan to the surgeon for review (e.g., step 508 of the method 500). This can include, for example, directly transmitting the virtual models and the surgical plan to the computing device 602 for surgeon review. In other embodiments, this can include uploading the virtual models and the surgical plan to the cloud 608. A surgeon can then download or otherwise access the virtual models and the surgical plan from the cloud 608 using the computing device 602.

The surgeon can use the computing device 602 to review the virtual models and the surgical plan. The surgeon can also approve or reject the surgical plan and provide any feedback regarding the surgical plan using the computing device 602. The surgeon's approval, rejection, and/or feedback regarding the surgical plan can be transmitted to, and received by, the computing system 606 (e.g., steps 512 and 514 of the method 500). The computing system 606 can than revise the virtual model and/or the surgical plan (e.g., step 516 of the method 500). The computing system 606 can transmit the revised virtual model and surgical plan to the surgeon for review (e.g., by uploading it to the cloud 608 or directly transmitting it to the computing device 602).

The computing system 606 can also design the patient-specific implant based on the corrected anatomical configuration and the surgical plan (e.g., step 508 of the method 500) using, the one or more software modules. In some embodiments, software modules rely on one or more algorithms, machine learning models, or other artificial intelligence architectures to design the implant.

The computing system 606 can also predict a probability and/or magnitude of subsidence of the patient-specific implant (e.g., step 510 of the method 500, steps 532-536 of the method 530). In some embodiments, the computing system 606 applies one or more software modules to predict the probability and/or magnitude of subsidence. The one or more software modules may rely on one or more algorithms, machine learning models, or other artificial intelligence architectures. Once the computing system 606 predicts the probability and/or magnitude of subsidence, the computing system 606 can transmit the predicted probability and/or magnitude to the surgeon for review, as described previously with reference to FIGS. 5A and 5B.

In some embodiments, the computing system 606 performs single or multilevel analyses to predict one or more characteristics of subsidence, such as maximum level of subsidence, rates of subsidence (e.g., subsidence at single level or along segment of spine or entire spine) distribution of subsidence (e.g., non-uniform subsidence, uniform subsidence) across an area or anatomical feature, level of subsidence (e.g., maximum predicted subsidence), subsidence related tilt, acceptable subsidence threshold, confidence levels of predictions, etc. The computing system 606 can modify implant dimensions (e.g., height, contact interface area) to compensate for the predicted subsidence, recommend ancillary procedures (e.g., procedures to prevent, limit, or compensate for subsidence), etc. In some embodiments, the computing system 606 can design an expandable implant configured to be expanded post-operatively to compensate for subsidence, thereby providing desired disk-height.

Once the computing system 606 designs the patient-specific implant, the computing system 606 can upload the design and/or manufacturing instructions to the cloud 608. The computing system 606 may also create fabrication instructions (e.g., computer-readable fabrication instructions) for manufacturing the patient-specific implant. In such embodiments, the computing system 606 can upload the fabrication instructions to the cloud 608. The manufacturing system 630 can download or otherwise access the design and/or fabrication instructions for the patient-specific implant from the cloud 608. The manufacturing system can then manufacture the patient-specific implant (e.g., step 518 in the method 500) using additive manufacturing techniques, subtractive manufacturing techniques, or other suitable manufacturing techniques.

The robotic surgical platform 650 can perform or otherwise assist with one or more aspects of the surgical procedure (e.g., step 520 of the method 500). For example, the platform 650 can prepare tissue for an incision, make an incision, make a resection, remove tissue, manipulate tissue, perform a corrective maneuver, deliver the implant to a target site, deploy the implant at the target site, adjust the implant at the target site, manipulate the implant once it is implanted, secure the implant at the target site, explant the implant, suture tissue, etc. The platform 650 can therefore include one or more arms 655 and end effectors for holding various surgical tools (e.g., graspers, clips, needles, needle drivers, irrigation tools, suction tools, staplers, screw driver assemblies, etc.), imaging instruments (e.g., cameras, sensors, etc.), and/or medical devices (e.g., the implant 600) and that enable the platform 650 to perform the one or more aspects of the surgical plan. Although shown as having one arm 655, one skilled in the art will appreciate that the platform 650 can have a plurality of arms (e.g., two, three, four, or more) and any number of joints, linkages, motors, and degrees of freedom. In some embodiments, the platform 650 may have a first arm dedicated to holding one or more imaging instruments, while the remainder of the arms hold various surgical tools. In some embodiments, the tools can be releasably secured to the arms such that they can be selectively interchanged before, during, or after an operative procedure. The arms can be moveable through a variety of ranges of motion (e.g., degrees of freedom) to provide adequate dexterity for performing various aspects of the operative procedure.

The platform 650 can include a control module 660 for controlling operation of the arm(s) 655. In some embodiments, the control module 660 includes a user input device (not shown) for controlling operation of the arm(s) 655. The user input device can be a joystick, a mouse, a keyboard, a touchscreen, an infrared sensor, a touchpad, a wearable input device, a camera- or image-based input device, a microphone, or other user input devices. A user (e.g., a surgeon) can interact with the user input device to control movement of the arm(s) 655.

In some embodiments, the control module 660 includes one or more processors for executing machine-readable operative instructions that, when executed, automatically control operation of the arm 655 to perform one or more aspects of the surgical procedure. In some embodiments, the control module 660 may receive the machine-readable operative instructions (e.g., from the cloud 608) specifying one or more steps of the surgical procedure that, when executed by the control module 660, cause the platform 650 to perform the one or more steps of the surgical procedure. For example, the machine-readable operative instructions may direct the platform 650 to prepare tissue for an incision, make an incision, make a resection, remove tissue, manipulate tissue, perform a corrective maneuver, deliver the implant 600 to a target site or region, deploy the implant 600 at the target site, adjust a configuration of the implant 600 at the target site, manipulate the implant 600 once it is implanted, secure the implant 600 at the target site, explant the implant 600, suture tissue, and the like. The operative instructions may therefor include particular instructions for articulating the arm 655 to perform or otherwise aid in the delivery of the patient-specific implant.

In some embodiments, the platform 650 can generate (e.g., as opposed to simply receiving) the machine-readable operative instructions based on the surgical plan. For example, the surgical plan can include information about the delivery path, tools, and implantation site. The platform 650 can analyze the surgical plan and develop executable operative instructions for performing the patient-specific procedure based on the capabilities (e.g., configuration and number of robotic arms, functionality of and effectors, guidance systems, visualization systems, etc.) of the robotic system. This enables the operative setup shown in FIG. 6 to be compatible with a wide range of different types of robotic surgery systems.

The platform 650 can include one or more communication devices (e.g., components having VLC, WiMAX, LTE, WLAN, IR communication, PSTN, Radio waves, Bluetooth, and/or Wi-Fi operability) for establishing a connection with the cloud 608 and/or the computing device 602 for accessing and/or downloading the surgical plan and/or the machine-readable operative instructions. For example, the cloud 608 can receive a request for a particular surgical plan from the platform 650 and send the plan to the platform 650. Once identified, the cloud 608 can transmit the surgical plan directly to the platform 650 for execution. In some embodiments, the cloud 608 can transmit the surgical plan to one or more intermediate networked devices (e.g., the computing device 602) rather than transmitting the surgical plan directly to the platform 650. A user can review the surgical plan using the computing device 602 before transmitting the surgical plan to the platform 650 for execution. Additional details for identifying, storing, downloading, and accessing patient-specific surgical plans are described in U.S. application Ser. No. 16/990,810, filed Aug. 11, 2020, the disclosure of which is incorporated by reference herein in its entirety.

The platform 650 can include additional components not expressly shown in FIG. 6. For example, in various embodiments the platform 650 may include one or more displays (e.g., LCD display screen, an LED display screen, a projected, holographic, or augmented reality display (e.g., a heads-up display device or a head-mounted device)), one or more I/O devices (e.g., a network card, video card, audio card, USB, firewire or other external device, camera, printer, speakers, CD-ROM drive, DVD drive, disk drive, or Blu-Ray device), and/or a memory (e.g., random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth). In some embodiments, the foregoing components can be generally similar to the like components described in detail with respect to computing device 200 in FIG. 2.

Without being bound by theory, using a robotic surgical platform to perform various aspects of the surgical plans described herein is expected to provide several advantages over conventional operative techniques. For example, use of robotic surgical platforms may improve surgical outcomes and/or shorten recovery times by, for example, decreasing incision size, decreasing blood loss, decreasing a length of time of the operative procedure, increasing the accuracy and precision of the surgery (e.g., the placement of the implant at the target location), and the like. The platform 650 can also avoid or reduce user input errors, e.g., by including one or more scanners for obtaining information from instruments (e.g., instruments with retrieval features), tools, the patient specific implant 600 (e.g., after the implant 600 has been gripped by the arm 655), etc. The platform 650 can confirm use of proper instruments prior and during the surgical procedure. If the platform 650 identifies an incorrect instrument or tool, an alert can be sent to a user that another instrument or tool should be installed. The user can scan the new instrument to confirm that the instrument is appropriate for the surgical plan. In some embodiments, the surgical plan includes instructions for use, a list of instruments, instrument specifications, replacement instruments, and the like. The platform 650 can perform pre- and post-surgical checking routines based on information from the scanners.

Figure 7:
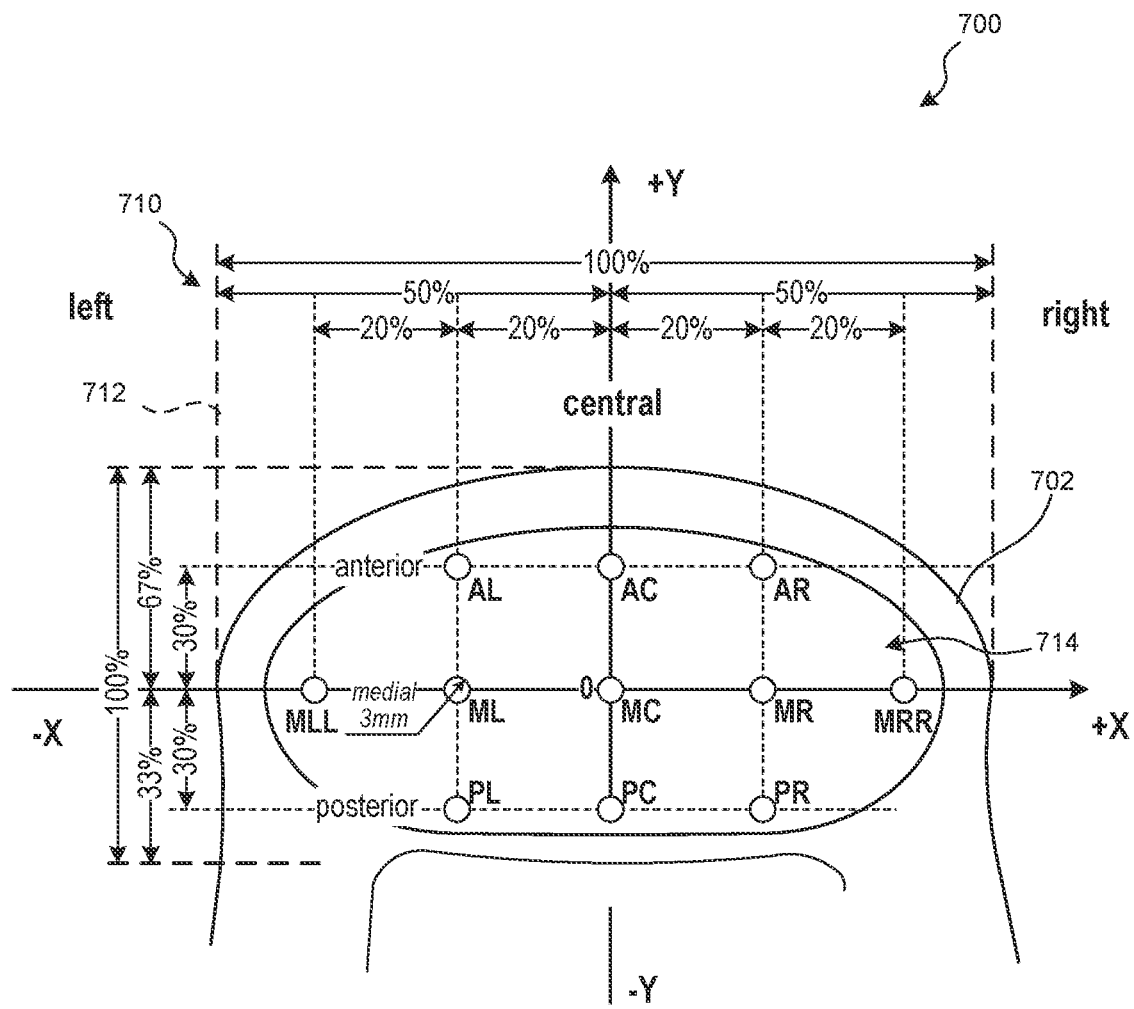
FIG. 7 illustrates an example virtual model of a portion of a patient's spine that can be used and/or generated in connection with the methods described herein, according to an embodiment.

FIGS. 7-10 further illustrate select aspects of providing patient-specific medical care, e.g., in accordance with the method 500. For example, FIG. 7 illustrates an example virtual model 700 of a portion of a patient's spine. In the illustrated embodiment, the virtual model 700 includes a vertebral body 702. The virtual model can be used to perform one or more simulations, such as mechanical simulations, bone growth simulations, subsidence predictions based on implant design, subsidence predictions based on vertebral properties, and/or any other tests or simulations described herein. In some embodiments, the virtual model 700 can include one or more regions. In the illustrated embodiment, for example, the virtual model 700 includes a grid 710 having a plurality of segment lines 712 in the lateral (e.g., "X") and the anterior-posterior (e.g., "Y") directions such that the grid 710 defines a plurality of regions 714 of the vertebral body 702. Each of the simulations described above can be performed on one or more of the regions 714. Although the regions 714 have a square shape in FIG. 7, in other embodiments the regions 714 can have a circular, curvilinear, rectilinear, triangular, rectangular, pentagonal, hexagonal, patient-specific, or any other suitable shape.

Figure 8:
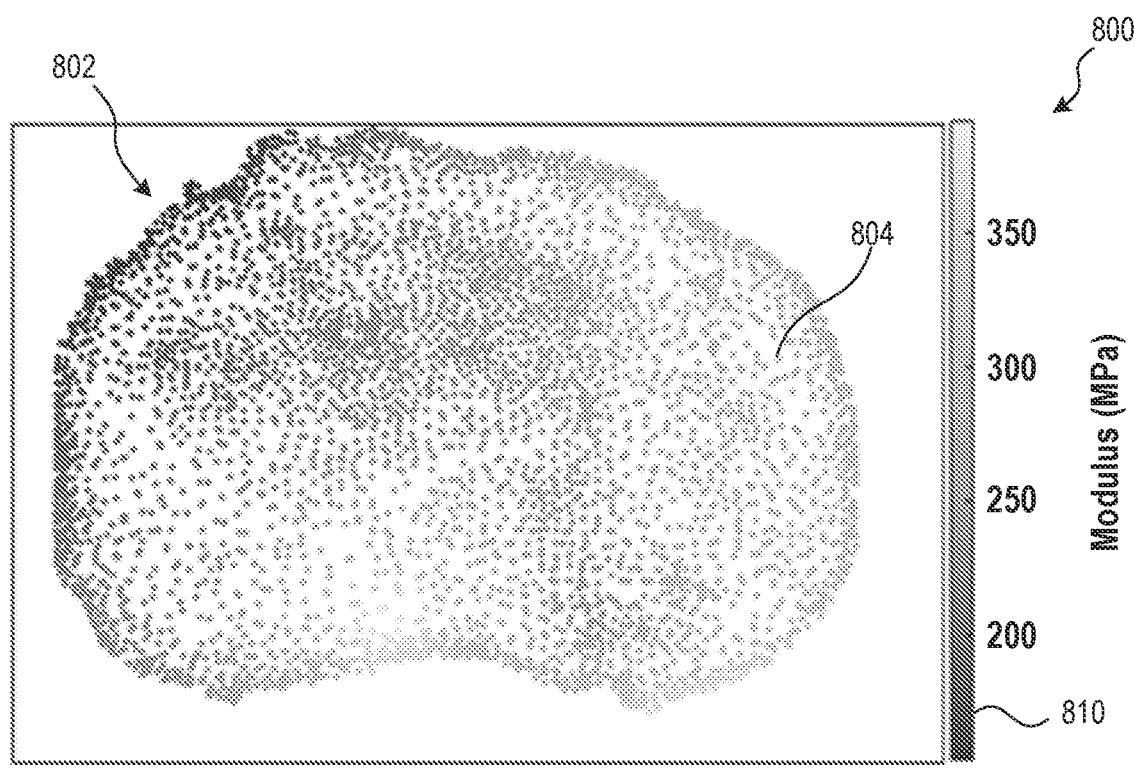
FIG. 8 illustrates another example virtual model of a portion of a patient's spine that can be used and/or generated in connection with the methods described herein, according to an embodiment.

FIG. 8 illustrates another example virtual model 800 of a portion of a patient's spine. The virtual model 800 can be generally similar to or the same as the virtual model 700 of FIG. 7. In the illustrated embodiment, however, the virtual model 800 includes stiffness data for a vertebral body 802. The stiffness data can be generated using one or more software modules, as described previously. The vertebral body 802 can be represented by a plurality of points 804, and each point 804 can be associated with a predicted stiffness value, for example, as shown by the gradient scale 810 in FIG. 8, in which lighter shades (e.g., white, light grey, etc.) correspond to areas of the vertebral body 802 having an increased relative stiffness, and darker shades (e.g., black, dark grey, etc.) correspond to areas of the vertebral body 802 having a decreased relative stiffness. As described previously, the predicted stiffness data can be used to predict a probability of subsidence and/or revise the design for one or more patient specific implants. For example, the patient-specific implants can be designed (and/or the design can be revised) such that the load-bearing portions of patient-specific implant are at least partially aligned with one or more portions of the vertebral body 802 having relatively increased stiffnesses or strength (e.g., as illustrated by a lighter or darker color in FIG. 8).

D. Select Embodiments of Patient-Specific Implants

Figure 9A:
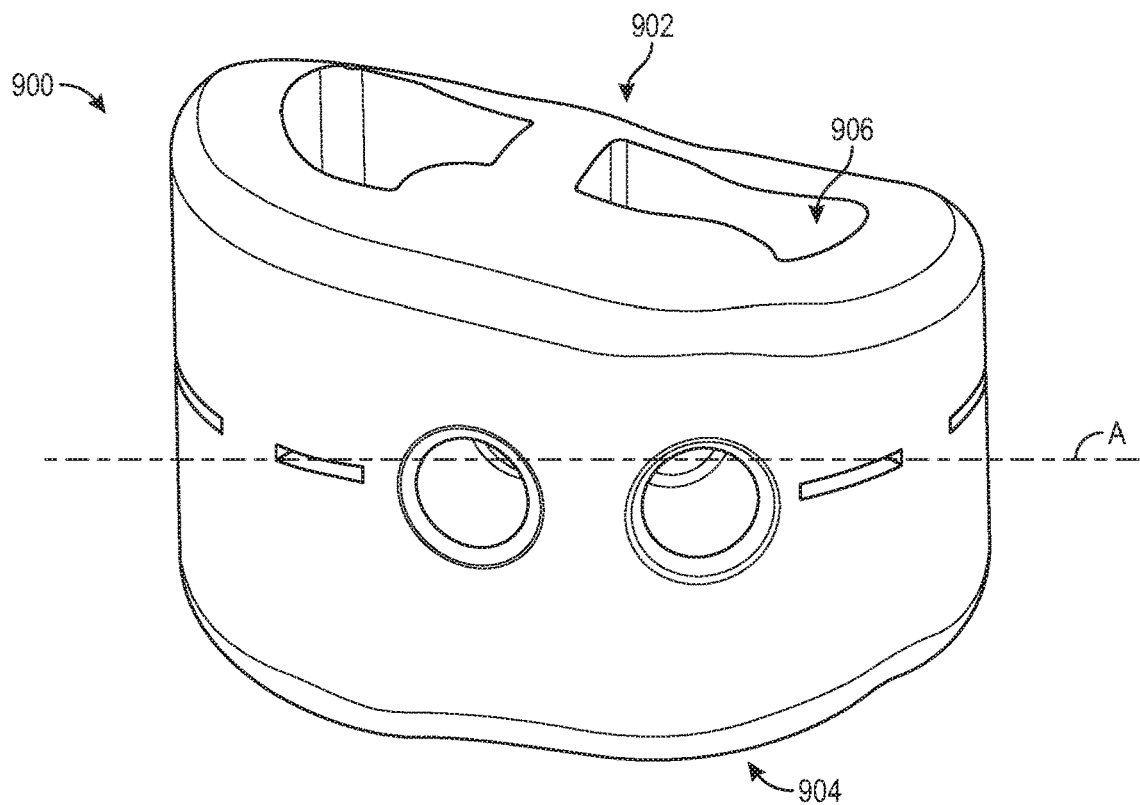
FIGS. 9A and 9B illustrate an exemplary patient-specific implant that can be used and/or generated in connection with the methods described herein, according to an embodiment.
Figure 9B:
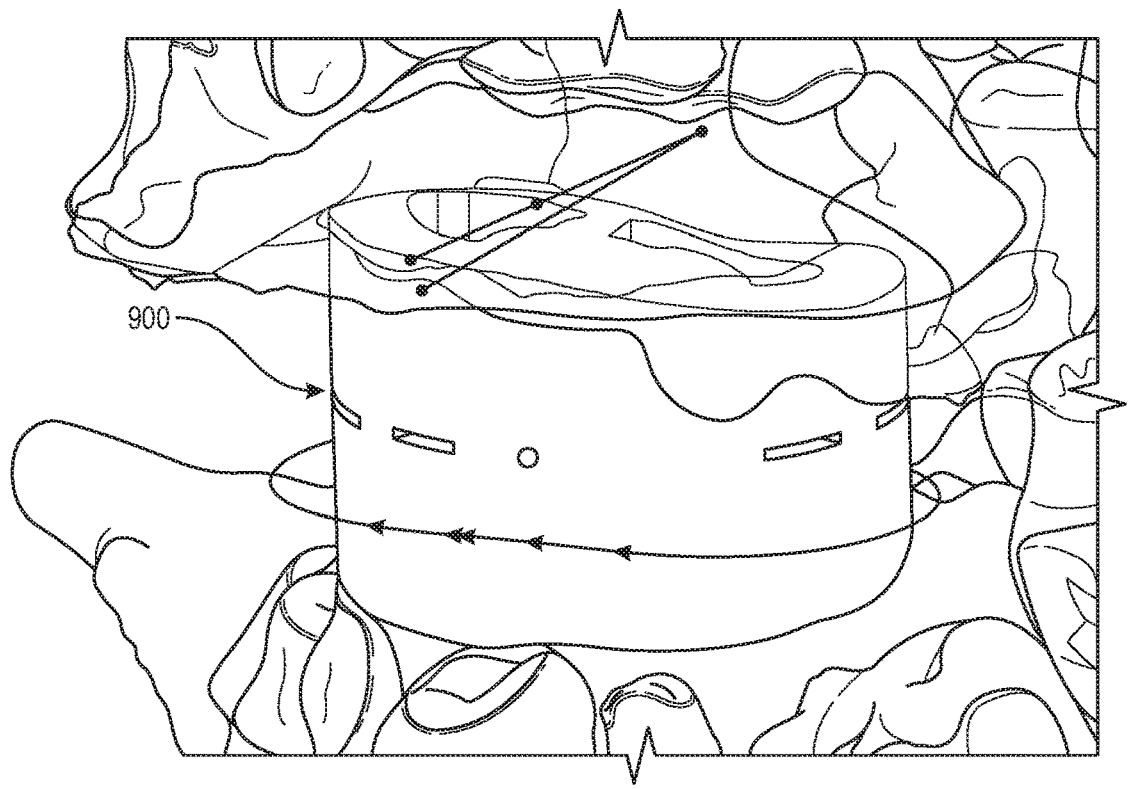

FIG. 9A illustrates an example of a patient-specific implant 900 (e.g., as designed in step 508 and manufactured in step 518 of the method 500), and FIG. 9B illustrates the implant 900 implanted in the patient. The implant 900 can be any orthopedic or other implant specifically designed to induce the patient's body to conform to the previously identified corrected anatomical configuration (e.g., step 504 of the method 500). In the illustrated embodiment, the implant 900 is an vertebral interbody device having a first (e.g., upper) surface 902 configured to engage an inferior endplate surface of a superior vertebral body and a second (e.g., lower) surface 904 configured to engage a superior endplate surface of an inferior vertebral body. The first surface 902 can have a patient-specific topography designed to match (e.g., mate with) the topography of the inferior endplate surface of the superior vertebral body to form a generally gapless interface therebetween. Likewise, the second surface 904 can have a patient-specific topography designed to match or mate with the topography of the superior endplate surface of the inferior vertebral body to form a generally gapless interface therebetween. The implant 900 may also include a recess 906 or other feature configured to promote bony ingrowth. Because the implant 900 is patient-specific and designed to induce a geometric change in the patient, the implant 900 is not necessarily symmetric, and is often asymmetric. For example, in the illustrated embodiment, the implant 900 has a non-uniform thickness such that a plane defined by the first surface 902 is not parallel to a central longitudinal axis A of the implant 900. Of course, because the implants described herein, including the implant 900, are patient-specific, the present technology is not limited to any particular implant design or characteristic. Additional features of patient-specific implants that can be designed and manufactured in accordance with the present technology are described in U.S. patent application Ser. Nos. 16/987,113 and 17/100,396, the disclosures of which are incorporated by reference herein in their entireties.

Figure 10:
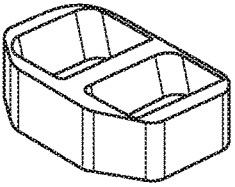
FIG. 10 illustrates a plurality of patient-specific implants that can be used and/or generated in connection with the methods described herein, according to an embodiment.

FIG. 10 illustrates a plurality of implants 1000 having variable patient-specific parameters. In the illustrated embodiment, for example, each of the implants 1000 can have a different geometry (e.g., contact surface area, patient-matching/conforming surface topography, etc.) and/or material property (e.g., porosity, stiffness, etc.). In some embodiments, the geometries and/or the material properties can be varied based on a predicted probability of subsidence and/or predicted magnitude of subsidence (e.g., steps 510, 512, and/or 513 of the method 500) and/or feedback from a surgeon (e.g., step 514 of the method 500). In some embodiments, the geometries and/or the material properties can be varied automatically based on the design parameters discussed previously regarding step 516 of the method 500. Although described as having varied geometries and/or material properties in FIG. 10, in these and other embodiments one or more other properties (e.g., length, width, stiffness, material type, shape, strength, flexibility, etc.) of the implants 1000 can be varied, for example, based on one or more of the parameters described herein and/or any other suitable parameter.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2018, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHOPEDIC IMPLANT FIXATION;"

U.S. application Ser. No. 16/383,215, filed on Apr. 12, 2019, titled "SYSTEMS AND METHODS FOR ORTHOPEDIC IMPLANT FIXATION;"

U.S. application Ser. No. 16/569,494, filed on Sep. 12, 2019, titled "SYSTEMS AND METHODS FOR ORTHOPEDIC IMPLANTS;" and U.S. application Ser. No. 16/699,447, filed Nov. 29, 2019, titled "SYSTEMS AND METHODS FOR ORTHOPEDIC IMPLANTS;"

U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS;"

U.S. application Ser. No. 17/100,396, filed Nov. 20, 2020, titled "PATIENT-SPECIFIC VERTEBRAL IMPLANTS WITH POSITIONING FEATURES;"

U.S. application Ser. No. 17/342,439, filed Jun. 8, 2021, titled "PATIENT-SPECIFIC MEDICAL PROCEDURES AND DEVICES, AND ASSOCIATED SYSTEMS AND METHODS;"

U.S. application Ser. No. 17/463,054, filed Aug. 31, 2021, titled "BLOCKCHAIN MANAGED MEDICAL IMPLANTS;"

U.S. application Ser. No. 17/531,417, filed Nov. 19, 2021, titled "PATIENT-SPECIFIC JIG FOR PERSONALIZED SURGERY;"

U.S. application Ser. No. 17/678,874, filed Feb. 23, 2022, titled "NON-FUNGIBLE TOKEN SYSTEMS AND METHODS FOR STORING AND ACCESSING HEALTHCARE DATA;"

U.S. application Ser. No. 17/835,777, filed Jun. 8, 2022, titled "PATIENT-SPECIFIC EXPANDABLE INTERVERTEBRAL IMPLANTS;"

U.S. application Ser. No. 17/842,242, filed Jun. 16, 2022, titled "PATIENT-SPECIFIC ANTERIOR PLATE IMPLANTS;"

U.S. application Ser. No. 17/851,487, filed Jun. 28, 2022, titled "PATIENT-SPECIFIC ADJUSTMENT OF SPINAL IMPLANTS, AND ASSOCIATED SYSTEMS AND METHODS;"

U.S. application Ser. No. 17/856,625, filed Jul. 1, 2022, titled "SPINAL IMPLANTS FOR MESH NETWORKS;"

U.S. application Ser. No. 17/867,621, filed Jul. 18, 2022, titled "PATIENT-SPECIFIC SACROILIAC IMPLANT, AND ASSOCIATED SYSTEMS AND METHODS;"

U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS;"

U.S. Application No. 63/274,135, filed Nov. 1, 2021, titled "PATIENT-SPECIFIC MEDICAL PROCEDURES AND DEVICES WITH IMPROVED SUBSIDENCE OUTCOMES, AND ASSOCIATED SYSTEMS AND METHODS;"

U.S. Application No. 63/274,300, filed Nov. 1, 2021, titled "PATIENT-SPECIFIC SPINAL INSTRUMENTS AND DECOMPRESSION SYSTEMS;"

U.S. Application No. 63/313,602, filed Feb. 24, 2022, titled "SYSTEMS AND METHODS FOR STORING AND ACCESSING HEALTHCARE DATA IN DIGITAL FILING CABINETS;"

U.S. Application No. 63/313,620, filed Feb. 24, 2022, titled "SYSTEMS AND METHODS FOR ANALYZING PATIENT-SPECIFIC HEALTHCARE DATA;"

U.S. Application No. 63/313,638, filed Feb. 24, 2022, titled "SYSTEMS AND METHODS FOR MANAGING PATIENT-SPECIFIC HEALTHCARE DATA BY A HEALTHCARE PROVIDER;" and U.S. Application No. 63/401,429, filed Aug. 26, 2022, titled "SYSTEMS AND METHODS FOR GENERATING, DESIGNING, AND/OR MODELING MULTIPLE PATIENT-SPECIFIC SURGICAL PLANS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method for providing patient-specific medical care, the method comprising:
  receiving patient data for a patient, the patient data including one or more images of the patient's spinal region showing the patient's native anatomical configuration;
  creating a virtual model of the spinal region showing the patient's native anatomical configuration;
  determining a corrected anatomical configuration of the patient's spinal region;
  updating the virtual model of the spinal region to illustrate the corrected anatomical configuration;
  designing one or more patient-specific intervertebral implants based on the updated virtual model;
  before manufacturing the one or more patient-specific intervertebral implants, predicting at least one of a probability that subsidence will occur and/or a magnitude of expected subsidence of the one or more patient-specific intervertebral implants, wherein the predicting is based at least in part on one or more mechanical properties of the patient's spinal region and/or one or more properties of the intervertebral implants; and
  in response to the predicted probability that subsidence will occur and/or the magnitude of expected subsidence being less than a predetermined threshold, generating fabrication instructions for making the one or more patient-specific intervertebral implants.

2. The computer-implemented method of claim 1 wherein predicting the probability of subsidence and/or the magnitude of subsidence includes:
  determining one or more mechanical properties of at least one vertebral body of the patient; and
  predicting bone growth of the at least one vertebral body relative to the patient-specific orthopedic implant.

3. The computer-implemented method of claim 2 wherein the mechanical properties include an endplate stiffness of the at least one vertebral body.

4. The computer-implemented method of claim 1 wherein the properties of the implant include a strength, stiffness, a length, a width, a contact surface area, a surface topography, a load-bearing surface position, and/or a target position of the patient-specific orthopedic implant.

5. The computer-implemented method of claim 1 wherein predicting the probability of subsidence and/or the magnitude of subsidence includes performing a simulation to model one or more interactions between the one or more patient-specific intervertebral implants and at least one vertebral body of the patient.

6. The computer-implemented method of claim 5 wherein the one or more interactions between the patient-specific orthopedic implant and at least one vertebral body include a force transfer, load sharing, and/or a change in orientation of at least a portion of the patient's spine.

7. The computer-implemented method of claim 1 wherein predicting the probability of subsidence and/or the magnitude of subsidence further includes comparing the patient data set and/or the one or more patient-specific intervertebral implants to a plurality of reference patient data sets to identify one or more similar patient data sets in the plurality of reference patient data sets, wherein each similar patient data set corresponds to a reference patient that (a) has similar spinal pathology data as the patient, (b) received treatment with a respective orthopedic implant, and (c) experienced a subsidence outcome associated with the respective orthopedic implant.

8. The computer-implemented method of claim 1 wherein predicting at least one of a probability that subsidence will occur and/or a magnitude of expected subsidence includes predicting the probability that subsidence will occur.

9. The computer-implemented method of claim 8 wherein the predetermined threshold is between about 5% and about 30%.

10. The computer-implemented method of claim 1 wherein predicting at least one of a probability that subsidence will occur and/or a magnitude of expected subsidence includes predicting the expected magnitude of subsidence.

11. The computer-implemented method of claim 10 wherein the predetermined threshold is between about 1 mm and about 5 mm.

12. The computer-implemented method of claim 1, further comprising in response to the predicted probability that subsidence will occur and/or the magnitude of expected subsidence being greater than the predetermined threshold, revising the design of the one or more patient-specific intervertebral implants.

13. The computer-implemented method of claim 12 wherein revising the design of the one or more patient-specific intervertebral implants includes (i) adjusting a stiffness of at least a portion of the patient-specific orthopedic implant, (ii) adjusting a contact surface area ratio between a surface of the patient-specific orthopedic implant and an endplate of a vertebral body of the patient, and/or (iii) aligning a load-bearing portion of the patient-specific orthopedic implant with a region of the vertebral body having one or more increased mechanical properties relative to at least one other region of the vertebral body.

14. A computer-implemented method for designing a patient-specific orthopedic implant, the method comprising:
receiving a patient data set of a patient, the patient data set including spinal pathology data for the patient;
comparing the patient data set to a plurality of reference patient data sets to identify one or more similar patient data sets in the plurality of reference patient data sets, wherein each similar patient data set corresponds to a reference patient that (a) has similar spinal pathology data as the patient, (b) received treatment with a respective orthopedic implant, and (c) experienced a subsidence outcome associated with the respective orthopedic implant;
selecting a subset of the one or more similar patient data sets, wherein each similar patient data set of the selected subset includes data indicating that the treatment with the respective orthopedic implant received by the reference patient produced a favorable subsidence outcome;
identifying, for at least one similar patient data set of the selected subset, design data for the respective orthopedic implant and surgical procedure data for a surgical procedure for implanting the respective orthopedic implant in the corresponding reference patient;
generating, based on the design data and the surgical procedure data, a design for the patient-specific orthopedic implant and a surgical procedure for implanting the patient-specific orthopedic implant in the patient;
predicting a probability of subsidence for the patient-specific orthopedic implant; and
revising the design for the patient-specific orthopedic implant and/or the surgical procedure based at least in part on the predicted probability of subsidence and one or more parameters associated with a reduced probability of subsidence.

15. The computer-implemented method of claim 14 wherein the probability of subsidence is based at least partially on the patient data and the design for the patient-specific orthopedic implant.

16. The computer-implemented method of claim 14 wherein predicting the probability of subsidence includes:
determining one or more mechanical properties of at least one vertebral body of the patient; and
predicting bone growth of the at least one vertebral body relative to the patient-specific orthopedic implant.

17. The computer-implemented method of claim 16 wherein the mechanical properties include an endplate stiffness of the at least one vertebral body.

18. The computer-implemented method of claim 14 wherein predicting the probability of subsidence includes performing a simulation to model one or more interactions between the patient-specific orthopedic implant and at least one vertebral body of the patient.

19. The computer-implemented method of claim 18 wherein the one or more interactions between the patient-specific orthopedic implant and at least one vertebral body include a force transfer, load sharing, and/or a change in orientation of at least a portion of the patient's spine.

20. The computer-implemented method of claim 14 wherein the one or more subsidence parameters include a stiffness, a length, a width, a contact surface area, a surface topography, a load-bearing surface position, and/or a target position of the patient-specific orthopedic implant.

21. The computer-implemented method of claim 20 wherein revising the design and/or the surgical procedure includes (i) adjusting a stiffness of at least a portion of the patient-specific orthopedic implant, (ii) increasing a contact surface area ratio between a surface of the patient-specific orthopedic implant and an endplate of a vertebral body of the patient, and/or (iii) aligning a load-bearing portion of the patient-specific orthopedic implant with a region of the vertebral body having an increased tolerance for loading.

22. A computer-implemented method for providing patient-specific medical care, the method comprising:
receiving patient data for a patient, the patient data including one or more images of the patient's spinal region showing the patient's native anatomical configuration;
determining a corrected anatomical configuration of the patient's spinal region;
generating a surgical plan for achieving the corrected anatomical configuration, the surgical plan including an identification of one or more vertebral levels to be involved in a surgical procedure for achieving the corrected anatomical configuration; and
designing one or more patient-specific virtual intervertebral implants that fit between vertebrae at the one or more vertebral levels to achieve the corrected anatomical configuration and are based at least partially on one or more subsidence design parameters,
wherein the one or more subsidence design parameters include a stiffness, a length, a width, a contact surface area, a surface topography, a load-bearing surface position, and/or a target position of each of the one or more patient-specific virtual intervertebral implants.

23. The computer-implemented method of claim 22 wherein designing the one or more patient-specific virtual intervertebral implants further includes predicting a probability of subsidence for at least one of the one or more patient-specific intervertebral implants.

24. The computer-implemented method of claim 23 wherein the probability of subsidence is based at least partially on the patient data and the designs for the one or more patient-specific virtual intervertebral implants.

25. The computer-implemented method of claim 23 wherein designing the one or more patient-specific virtual intervertebral implants includes:
predicting one or more mechanical properties of the vertebrae; and predicting bone growth of the vertebrae relative to the one or more patient-specific virtual intervertebral implants.

26. The computer-implemented method of claim 25 wherein the mechanical properties include an endplate strength or stiffness of the vertebrae.

27. The computer-implemented method of claim 22 wherein designing the one or more patient-specific virtual intervertebral implants includes performing a simulation to model one or more interactions between the one or more patient-specific virtual intervertebral implant and the corresponding vertebrae.

28. The computer-implemented method of claim 27 wherein the one or more interactions between the patient-specific virtual intervertebral implants and the corresponding vertebrae include a force transfer, a load sharing, and/or an orientation of a portion of the patient's spine.

29. The computer-implemented method of claim 22, wherein designing the one or more patient-specific virtual intervertebral implants includes: (i) generating a first design for each of the one or more patient-specific virtual intervertebral implants, (ii) predicting a probability and/or a magnitude of subsidence for at least one of the first designs, and (iii) revising one or more of the first designs based at least in part on the predicted probability and/or magnitude of subsidence and the one or more subsidence parameters to generate a second design having a decreased predicted probability and/or magnitude of subsidence.

30. The computer-implemented method of claim 29 wherein revising the design and/or the surgical procedure includes (i) adjusting a stiffness of at least a portion of the patient-specific intervertebral implants and/or (ii) increasing a contact surface area ratio between a surface of the patient-specific intervertebral implants and an endplate of the vertebrae.

31. The computer-implemented method of claim 22 wherein generating the surgical plan includes: (i) generating a first surgical plan, (ii) predicting a probability and/or a magnitude of subsidence for the first surgical plan, and (iii) revising the first surgical plan based at least in part on the predicted probability and/or magnitude of subsidence to generate a second surgical plan having a decreased predicted probability and/or magnitude of subsidence.

32. The computer-implemented method of claim 31 wherein revising the surgical plan includes aligning a load-bearing portion of at least one of the patient-specific virtual interverbal implants with a region of the corresponding vertebrae having an increased stiffness.

33. A system for generating a patient-specific orthopedic implant, the system comprising:
one or more processors; and
a memory storing instructions that, when executed by the one or more processors, cause the system to perform operations comprising:
receiving a patient data set of a patient;
comparing the patient data set to a plurality of reference patient data sets, wherein each of the plurality of reference patient data sets is associated with a corresponding reference patient;
selecting a subset of the plurality of reference patient data sets based, at least partly, on similarity to the patient data set and subsidence outcome of the corresponding reference patient; and
generating, based on the selected subset, at least one patient-specific orthopedic implant design for treating the patient.

34. The system of claim 33 wherein generating the design includes predicting a probability of subsidence for the at least one patient-specific orthopedic implant.

35. The system of claim 34 wherein the probability of subsidence is based at least partially on the patient data and the generated design for the at least one patient-specific orthopedic implant.

36. The system of claim 33 wherein generating the design includes:
predicting one or more mechanical properties of at least one vertebrae of the patient; and
predicting bone growth of the at least one vertebra relative to the at least one patient-specific orthopedic implant.

37. The system of claim 36 wherein the mechanical properties include an endplate strength or stiffness of the at least one vertebra.

38. The system of claim 33 wherein generating the design includes performing a simulation to model one or more interactions between the at least one patient-specific orthopedic implant and at least one corresponding vertebra of the patient.

39. The system of claim 38 wherein the one or more interactions between the at least one patient-specific orthopedic implant and the at least one corresponding vertebra of the patient include a force transfer, a load sharing, and/or an orientation of a portion of the patient's spine.

40. The system of claim 33 wherein generating the design includes generating the design based at least in part on one or more subsidence-mitigating design parameters.

41. The system of claim 40 wherein the one or more subsidence-mitigating design parameters include a strength, stiffness, a length, a width, a contact surface area, a surface topography, a load-bearing surface position, and/or a target position of each of the at least one patient-specific orthopedic implant.

42. The system of claim 33 wherein generating the design includes simulating subsidence at multiple levels along the patient's spine.

43. The system of claim 33 wherein the patient data set includes a subset of reference patient data with spinal curvatures similar to the patient, the method further comprising selecting one or more levels along the patient's spine based on the subset of reference patient data with spinal curvatures similar to the patient.

44. A computer-implemented method of providing patient-specific surgical care, the method comprising:
receiving a proposed surgical plan for a patient, the proposed surgical plan including at least one surgical procedure to be performed on the patient and parameters for at least one implant to be implanted in the patient;
comparing the proposed surgical plan with one or more patient tissue characteristics to determine a probability of and/or predicted magnitude of subsidence following execution of the proposed surgical plan;
in response to the probability of and/or predicted magnitude of subsidence being equal to or greater than a predetermined threshold, indicating that one or more aspects of the proposed surgical plan need to be modified to reduce the probability of and/or predicted magnitude of subsidence; and
in response to the probability of and/or predicted magnitude of subsidence being less than the predetermined threshold, indicating that the proposed surgical plan complies with acceptable subsidence parameters.

45. The computer-implemented method of claim 44 wherein the predetermined threshold is a threshold magnitude of subsidence, and wherein:
- in response to the predicted magnitude of subsidence being equal to or greater than the threshold magnitude, indicating that one or more aspects of the proposed surgical plan need to be modified; and
- in response to the predicted magnitude of subsidence being less than the threshold magnitude, indicating that the proposed surgical plan complies with acceptable subsidence parameters.

46. The computer-implemented method of claim 45 wherein the threshold magnitude is between about 1 mm and about 5 mm.

47. The computer-implemented method of claim 44 wherein the predetermined threshold is a probability of subsidence, and wherein:
- in response to the probability of subsidence being equal to or greater than the threshold probability, indicating that one or more aspects of the proposed surgical plan need to be modified; and
- in response to the probability of subsidence being less than the threshold probability, indicating that the proposed surgical plan complies with acceptable subsidence parameters.

48. The computer-implemented method of claim 47 wherein the threshold probability is between about 5% and about 30%.

49. A system for providing patient-specific surgical care, the system comprising:
- one or more processors; and
- a memory storing instructions that, when executed by the one or more processors, cause the system to perform operations comprising:
  - receiving a proposed surgical plan for a patient, the proposed surgical plan including at least one surgical procedure to be performed on the patient and parameters for at least one implant to be implanted in the patient;
  - comparing the proposed surgical plan with one or more patient tissue characteristics to determine a probability of and/or predicted magnitude of subsidence following execution of the proposed surgical plan;
  - in response to the probability of and/or predicted magnitude of subsidence being equal to or greater than a predetermined threshold, indicating that one or more aspects of the proposed surgical plan need to be modified to reduce the probability of and/or predicted magnitude of subsidence; and
  - in response to the probability of and/or predicted magnitude of subsidence being less than the predetermined threshold, indicating that the proposed surgical plan complies with acceptable subsidence parameters.

50. The system of claim 49 wherein the predetermined threshold is a threshold magnitude of subsidence, and wherein the operations comprise:
- in response to the predicted magnitude of subsidence being equal to or greater than the threshold magnitude, indicating that one or more aspects of the proposed surgical plan need to be modified; and
- in response to the predicted magnitude of subsidence being less than the threshold magnitude, indicating that the proposed surgical plan complies with acceptable subsidence parameters.

51. The system of claim 50 wherein the threshold magnitude is between about 1 mm and about 5 mm.

52. The system of claim 49 wherein the predetermined threshold is a probability of subsidence, and wherein the operations comprise:
- in response to the probability of subsidence being equal to or greater than the threshold probability, indicating that one or more aspects of the proposed surgical plan need to be modified; and
- in response to the probability of subsidence being less than the threshold probability, indicating that the proposed surgical plan complies with acceptable subsidence parameters.

53. The system of claim 52 wherein the threshold probability is between about 5% and about 30%.

54. The system of claim 49 wherein at least the operation of comparing the proposed surgical plan with one or more patient tissue characteristics to determine a probability of and/or predicted magnitude of subsidence following execution of the proposed surgical plan is performed using a trained machine learning and/or artificial intelligence model.

* * * * *

UNITED STATES PATENT AND TRADEMARK OFFICE
CERTIFICATE OF CORRECTION

PATENT NO. : 12,390,276 B2  
APPLICATION NO. : 17/978673  
DATED : August 19, 2025  
INVENTOR(S) : Jeremy Winston et al.

Page 1 of 1

It is certified that error appears in the above-identified patent and that said Letters Patent is hereby corrected as shown below:

On the Title Page
1. On Page 4, item (56), under "OTHER PUBLICATIONS", in Column 2, Lines 15-16, delete "www. materialize.com/en/medical/software/mimics," and insert --www.materialize.com/en/medical/software/mimics,--

In the Specification
2. In Column 4, Line 34, delete "angels," and insert --angles,--
3. In Column 4, Line 53, delete "angels," and insert --angles,--
4. In Column 7, Line 23, delete "pathology, condition," and insert --pathology,--
5. In Column 11, Line 35, delete "health-care" and insert --healthcare--
6. In Column 13, Line 45, delete "based the" and insert --based on the--
7. In Column 15, Line 42, delete "make" and insert --to make--
8. In Column 17, Line 43, delete "more" and insert --or more--
9. In Column 17, Line 44, delete "out of" and insert --out--
10. In Column 22, Line 21, delete "according" and insert --according to--
11. In Column 26, Line 17, delete "that that," and insert --that,--
12. In Column 27, Line 49, delete "change" and insert --chance--
13. In Column 30, Line 31, delete "motion" and insert --motion of--
14. In Column 35, Line 64, delete "than" and insert --then--
15. In Column 40, Line 66, delete "and or" and insert --and/or--

In the Claims
16. In Column 47, Line 48, in Claim 32, delete "interverbal" and insert --intervertebral--
17. In Column 48, Line 12, in Claim 36, delete "vertebrae" and insert --vertebra--

Signed and Sealed this  
Second Day of December, 2025

John A. Squires  
*Director of the United States Patent and Trademark Office*